US011513332B2

(12) United States Patent
Ishikawa et al.

(10) Patent No.: US 11,513,332 B2
(45) Date of Patent: Nov. 29, 2022

(54) MICROSCOPE APPARATUS AND CONTROL METHOD

(71) Applicant: Sony Olympus Medical Solutions Inc., Tokyo (JP)

(72) Inventors: Tomonori Ishikawa, Tokyo (JP); Noboru Shibuya, Tokyo (JP); Yoshia Hoshino, Tokyo (JP); Takashi Fukaya, Tokyo (JP); Masaaki Ueda, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 658 days.

(21) Appl. No.: 16/462,938

(22) PCT Filed: Sep. 8, 2017

(86) PCT No.: PCT/JP2017/032402
§ 371 (c)(1),
(2) Date: May 22, 2019

(87) PCT Pub. No.: WO2018/100828
PCT Pub. Date: Jun. 7, 2018

(65) Prior Publication Data
US 2020/0064615 A1    Feb. 27, 2020

(30) Foreign Application Priority Data
Nov. 29, 2016    (JP) .............................. JP2016-231680

(51) Int. Cl.
*G02B 21/36*    (2006.01)
*G02B 21/08*    (2006.01)
*G02B 21/24*    (2006.01)

(52) U.S. Cl.
CPC ......... *G02B 21/362* (2013.01); *G02B 21/082* (2013.01); *G02B 21/241* (2013.01)

(58) Field of Classification Search
CPC .. G02B 21/362; G02B 21/082; G02B 21/241; G02B 21/0012; G02B 21/06; A61B 90/25; A61B 3/13; A61F 9/007
(Continued)

(56) References Cited

U.S. PATENT DOCUMENTS 5,748,366 A     5/1998  Yasunaga et al.
7,268,938 B2 *  9/2007  Kawano .............. G02B 21/0012
                                                  359/368
(Continued)

FOREIGN PATENT DOCUMENTS

DE    202009000778 U1    3/2009
JP       61-100713 A       5/1986
(Continued)

OTHER PUBLICATIONS

International Search Report and Written Opinion dated Nov. 28, 2017 for PCT/JP2017/032402 filed on Sep. 8, 2017, 12 pages including Translation of the International Search Report.
(Continued)

*Primary Examiner* — Stephone B Allen
*Assistant Examiner* — Rahman Abdur
(74) *Attorney, Agent, or Firm* — Xsensus LLP

(57) ABSTRACT

Provided is a microscope apparatus including: a microscope section configured to perform magnified observation of a subject's eye while obtaining a red reflex caused by irradiating a fundus of the subject's eye with illuminating light; a holding section configured to hold the microscope section; and a tilting section configured to tilt an illumination optical axis which is an optical axis of an illumination optical system, and an observation optical axis which is an optical axis of an observation optical system in the microscope section, around a tilt reference point in an interior of the subject's eye as a base point, while maintaining a substan-
(Continued)

tially coaxial state between the illumination optical axis and the observation optical axis.

20 Claims, 22 Drawing Sheets

(58) Field of Classification Search
 USPC .................................................. 359/382, 368
 See application file for complete search history.

(56) References Cited

U.S. PATENT DOCUMENTS

| | | | | |
|---|---|---|---|---|
| 8,456,739 | B2* | 6/2013 | Stuettler | ............... A61B 90/25 359/390 |
| 2005/0237604 | A1* | 10/2005 | Kawano | ............... G02B 21/082 359/368 |
| 2007/0024965 | A1 | 2/2007 | Sander | |

FOREIGN PATENT DOCUMENTS

| | | | | | |
|---|---|---|---|---|---|
| JP | 3-182239 | A | | 8/1991 | |
| JP | 5-253246 | A | | 10/1993 | |
| JP | H06315487 | A | | 11/1994 | |
| JP | 7-113959 | A | | 5/1995 | |
| JP | 8-266555 | A | | 10/1996 | |
| JP | 2001-108906 | A | | 4/2001 | |
| JP | 2004-255177 | A | | 9/2004 | |
| JP | 2007034301 | A | | 2/2007 | |
| JP | 2007097650 | | * | 4/2007 | ............... A61B 3/13 |
| JP | 2010-179143 | A | | 8/2010 | |
| JP | 2010179143 | | * | 8/2010 | ............. G02B 21/20 |
| JP | 2013-56204 | A | | 3/2013 | |
| JP | 6217890 | B1 | | 10/2017 | |
| WO | 2016/017532 | A1 | | 2/2016 | |

OTHER PUBLICATIONS

Extended Search Report issued in European Application 17875516. 1-1124 dated Oct. 24, 2019.

* cited by examiner

MICROSCOPE APPARATUS AND CONTROL METHOD

CROSS-REFERENCE TO RELATED APPLICATIONS

The present application is based on PCT filing PCT/JP2017/032402, filed Sep. 8, 2017 which claims priority to JP 2016-231680, filed Nov. 29, 2016, the entire contents of each are incorporated herein by reference.

TECHNICAL FIELD

The present disclosure relates to a microscope apparatus and a control method.

BACKGROUND ART

A microscope apparatus used for eye surgery (hereinafter also called simply a microscope apparatus) is known as an apparatus for providing a surgeon with a magnified image of an eye of a patient (subject's eye) to enable delicate procedures. For example, as described in Patent Literature 1, a microscope apparatus includes a microscope section provided with an illumination optical system and an observation optical system, an arm section (holding section) for moving and holding the microscope, an X-Y apparatus for moving the microscope section in the horizontal plane, and operating means such as a footswitch for operating the X-Y apparatus and the like. Note that the above X-Y apparatus is used to move a desired site of observation in the subject's eye to the center of the field of view in the case of changing the site where a procedure is performed, in the case in which the subject's eye has moved, and the like, for example.

Meanwhile, in cataract surgery, because it is necessary to clearly observe a transparent body, namely the crystalline lens, it is typical to obtain reflected light (hereinafter designated the red reflex) from the fundus (retina) by irradiating the interior of the eye from the pupil of the subject's eye with illuminating light from the illumination optical system of the microscope apparatus, and utilize the red reflex as a backlight for crystalline lens observation (see Patent Literature 2, for example). To obtain the red reflex favorably, it is necessary to irradiate the subject's eye with illuminating light from substantially the front while also observing the reflected light from the fundus substantially in front of the subject's eye (in other words, the eye axis of the subject's eye and the optical axis of the illumination optical system (illumination optical axis) are substantially aligned, while in addition, the eye axis of the subject's eye and optical axis of the observation optical system of the microscope section (observation optical axis) are substantially aligned).

On the other hand, since cataract surgery typically is performed under local anesthesia, the subject's eye often moves during surgery due to the patient's own movements. In addition, movement in the subject's eye also occurs because of treatment operations by the surgeon. Note that since the patient's head basically does not move, these movements of the subject's eye are movements that tilt the eye axis. In the case in which the subject's eye moves in this way, a change occurs in the relative angle between the eye axis of the subject's eye and the illumination optical axis, and the illuminating light becomes less likely to irradiate the fundus, causing a loss of the red reflex that had been obtained up to that point, and making observation of the crystalline lens difficult. Consequently, in the case in which subject's eye has moved, the surgeon must suspend treatment of the subject's eye and perform work to move the microscope section to search for a state in which the red reflex is obtained favorably while observing an image of the subject's eye. Such a situation not only leads to longer surgery time, but is also a factor that increases the burden on the surgeon.

Note that if the X-Y apparatus described above is used, the microscope section can be moved more smoothly, and there is a possibility of being able to reduce the burden on the surgeon when moving the microscope section. However, whereas the movement of the microscope section by the X-Y apparatus is movement in the horizontal plane, as described above, the movement of the subject's eye is a motion that tilts the eye axis. Consequently, even if the microscope section is moved by the X-Y apparatus, there is a low possibility of obtaining a favorable red reflex.

Accordingly, there is being developed technology that controls the observation state automatically according to the movement of the subject's eye such that a favorable red reflex is obtained in surgery using a microscope apparatus. For example, Patent Literature 3 to 5 disclose technologies that detect the brightness of the red reflex and control the intensity of the illuminating light on the basis of the detection result. With these technologies, in the case in which the brightness of the red reflex falls in association with the movement of the subject's eye, the intensity of the illuminating light is strengthened such that the brightness of the red reflex becomes greater. In addition, Patent Literature 3 to 5 also disclose technologies that detect the brightness of the red reflex and change the angle of the illumination optical axis with respect to the observation optical axis on the basis of the detection result. With these technologies, in the case in which the brightness of the red reflex falls in association with the movement of the subject's eye, the direction of the illumination optical axis is changed such that the subject's eye is irradiated favorably by the illuminating light.

CITATION LIST

Patent Literature

Patent Literature 1: JP H3-182239A
Patent Literature 2: JP S61-100713A
Patent Literature 3: JP 2010-179143A
Patent Literature 4: JP 2013-56204A
Patent Literature 5: JP 2004-255177A

DISCLOSURE OF INVENTION

Technical Problem

However, with regard to the above technologies that control the intensity of the illuminating light, strengthening the intensity of the illuminating light increases the invasion of light into the subject's eye, and therefore is undesirable to the patient. On the other hand, as also described in Patent Literature 2, the importance of the relative angle between the illumination optical axis and the observation optical axis to obtain a favorable red reflex and observe the crystalline lens clearly has been confirmed. With the above technologies that change the angle of the illumination optical axis with respect to the observation optical axis, contrary to the above finding, since the relationship between the illumination optical axis and the observation optical axis is changed, an advantageous effect may not necessarily be expected.

In light of the above circumstances, in eye surgery using a microscope apparatus, there is demand for a technology whereby a favorable red reflex is obtained more appropriately even in cases in which the subject's eye moves, making it possible to perform surgery more smoothly. Accordingly, the present disclosure proposes and novel and improved microscope apparatus and control method making it possible to perform eye surgery more smoothly.

Solution to Problem

According to the present disclosure, there is provided a microscope apparatus including: a microscope section configured to perform magnified observation of a subject's eye while obtaining a red reflex caused by irradiating a fundus of the subject's eye with illuminating light; a holding section configured to hold the microscope section; and a tilting section configured to tilt an illumination optical axis which is an optical axis of an illumination optical system, and an observation optical axis which is an optical axis of an observation optical system in the microscope section, around a tilt reference point in an interior of the subject's eye as a base point, while maintaining a substantially coaxial state between the illumination optical axis and the observation optical axis.

Moreover, according to the present disclosure, there is provided a control method, executed by a process, including: when using a microscope apparatus provided with a microscope section and a holding section to perform magnified observation of a subject's eye by the microscope section while obtaining a red reflex caused by irradiating the subject's eye with illuminating light, tilting an illumination optical axis which is an optical axis of an illumination optical system, and an observation optical axis which is an optical axis of an observation optical system in the microscope section, around a tilt reference point in an interior of the subject's eye as a base point, while maintaining a substantially coaxial state between the illumination optical axis and the observation optical axis, according to a motion of the subject's eye.

According to the present disclosure, a microscope apparatus is provided with a tilting section that tilts the illumination optical axis and the observation optical axis while maintaining a substantially coaxial state between the illumination optical axis and the observation optical axis, treating a tilt reference point inside the subject's eye as a base point. Consequently, in the case in which the subject's eye moves (tilts) during surgery, if the illumination optical axis and the observation optical axis are tilted by the tilting section in the direction that the subject's eye has moved, immediately after tilting, a state is obtained in which the illumination optical axis and the observation optical axis already are substantially coaxial and incident on the subject's eye from substantially the front. In other words, immediately after tilting the illumination optical axis and the observation optical axis by the tilting section, a favorable red reflex is obtained promptly, making it possible to continue clear observation of the crystalline lens by the microscope section. Consequently, smoother surgery may be achieved.

Advantageous Effects of Invention

Note that the effects described above are not necessarily limitative. With or in the place of the above effects, there may be achieved any one of the effects described in this specification or other effects that may be grasped from this specification

MODE(S) FOR CARRYING OUT THE INVENTION

Figure 1:
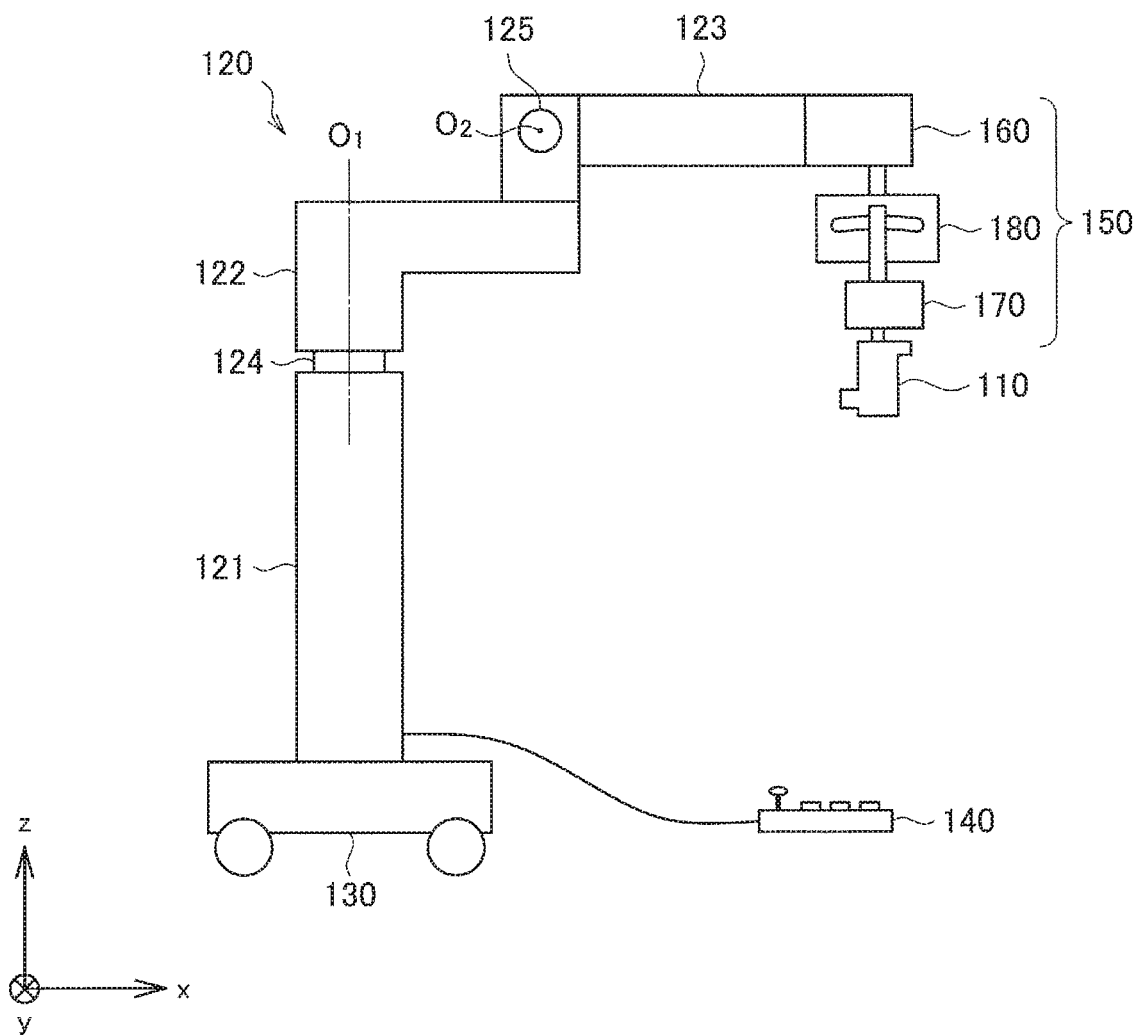
FIG. 1 is a diagram schematically illustrating an overall configuration of a microscope apparatus according to a first embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that in each of the diagrams illustrated in this specification, the apparent sizes of some component members are exaggerated in some cases for the sake of explanation. The relative sizes of the respective members illustrated in each of the drawings do not necessarily represent accurately the size relationships among actual members.

Also, in the following description, when describing the configuration of the arm section (holding section) of the microscope apparatus, the side where the microscope section is provided will also be called the front end side or the like, while the side close to the base section will also be called the base end side or the like.

Also, in this specification, the "tilting (operation) of the microscope section" means an operation in which the microscope section moves such that its optical axis (illumination optical axis and observation optical axis) tilts by treating a predetermined point on the optical axis as a reference. For example, an operation of the microscope section whereby the direction of the optical axis changes due to the microscope section rotating about a rotation axis that passes through the microscope section (for example, an operation of the microscope section by the elevation apparatus 270 in the second embodiment) will not be described as a "tilt", but instead be described as a "rotation of the microscope section".

Hereinafter, the description will proceed in the following order.

1. First embodiment
1-1. Configuration of microscope apparatus
1-2. Operations of microscope apparatus
1-3. Functional configuration
1-4. Control method
1-5. Modification
2. Second embodiment
2-1. Configuration of microscope apparatus
2-2. Operations of microscope apparatus
2-3. Modification
3. Third embodiment
3-1. Configuration of microscope apparatus
3-2. Operations of microscope apparatus
4. Supplement

1. First Embodiment (1-1. Configuration of Microscope Apparatus)

Figure 2:
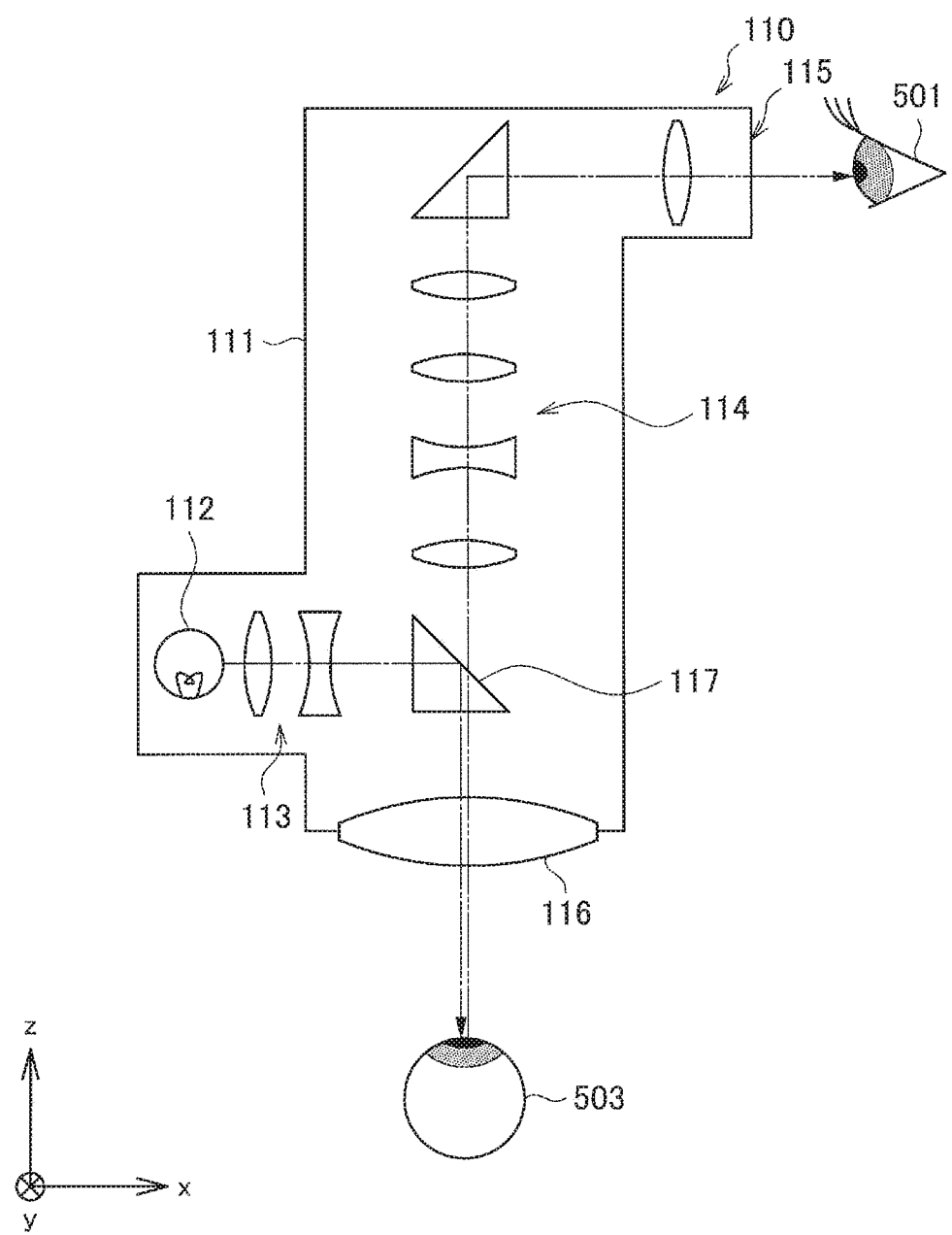
FIG. 2 is a cross-section diagram schematically illustrating a configuration of a microscope section of the microscope apparatus illustrated in FIG. 1.
Figure 3:
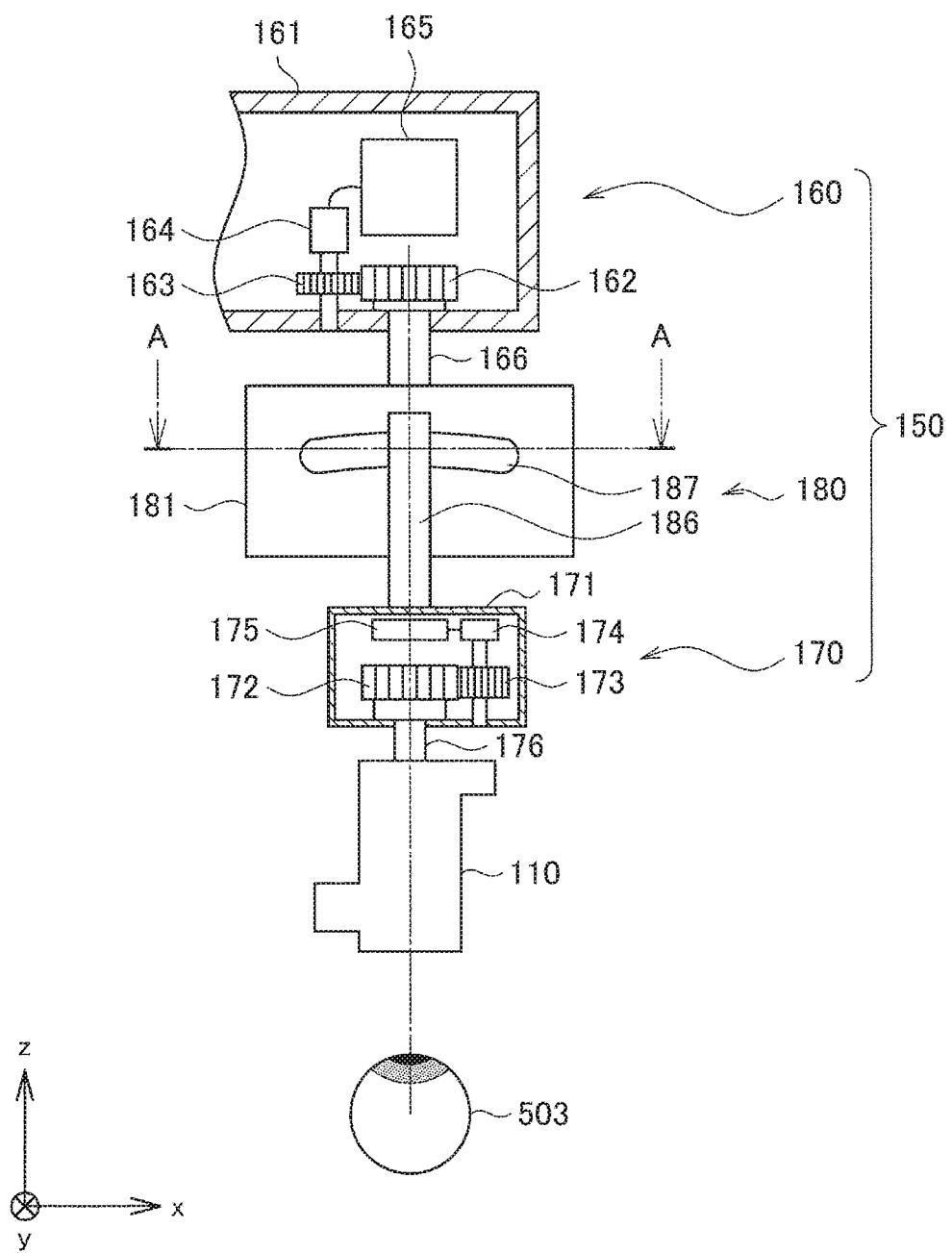
FIG. 3 is a diagram schematically illustrating a configuration of a tilting section of the microscope apparatus illustrated in FIG. 1.
Figure 4:
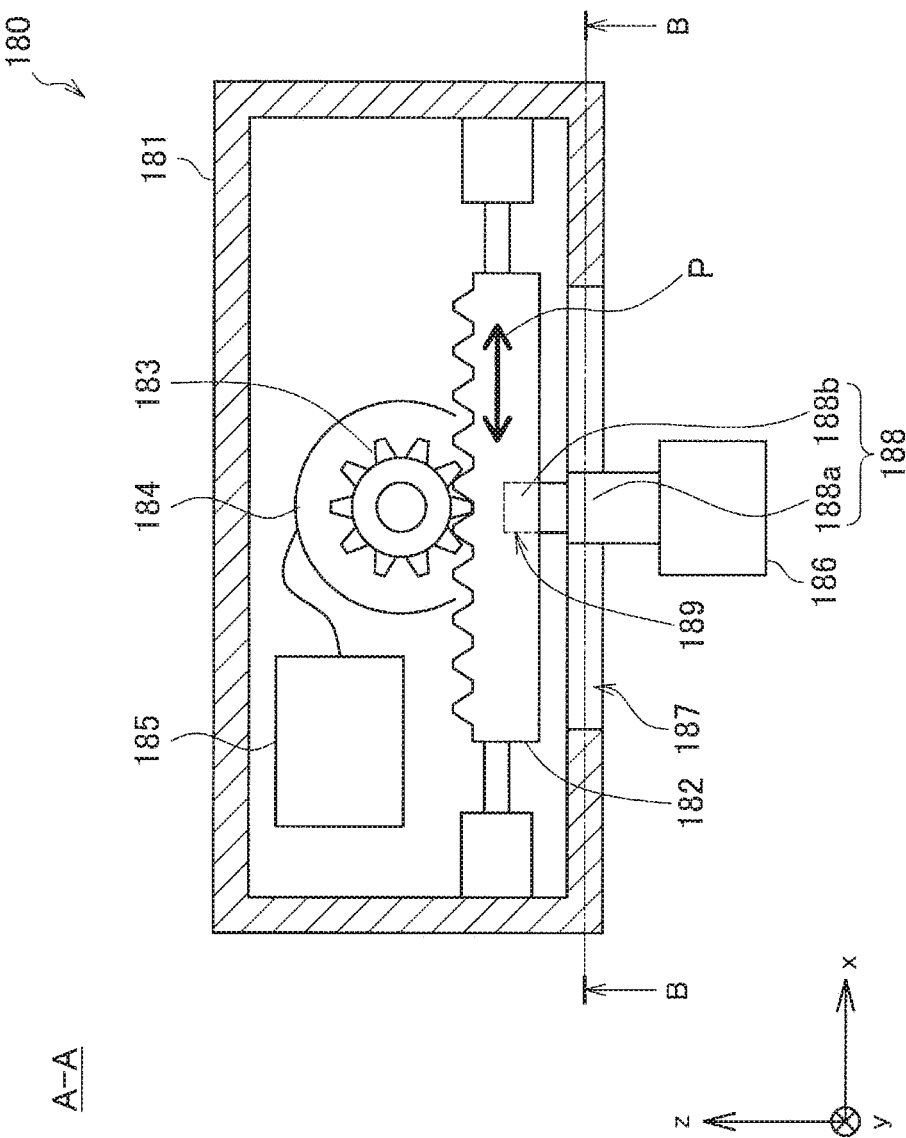
FIG. 4 is a cross-section diagram schematically illustrating the state of the A-A cross-section of a tilt driving mechanism included in the tilting section illustrated in FIG. 3.
Figure 5:
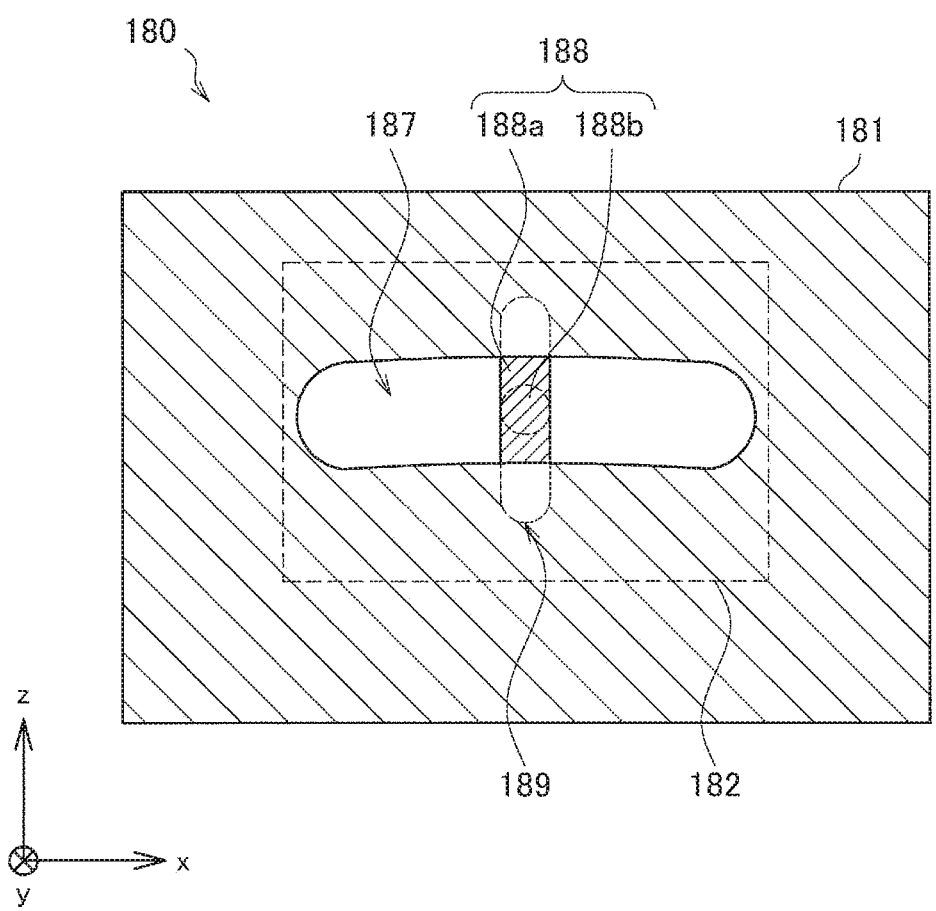
FIG. 5 is a cross-section diagram schematically illustrating the state of the B-B cross-section of the tilt driving mechanism illustrated in FIG. 4.

FIGS. 1 to 5 will be referenced to describe a configuration of the microscope apparatus according to the first embodiment of the present disclosure. FIG. 1 is a diagram schematically illustrating an overall configuration of the microscope apparatus according to the first embodiment. FIG. 2 is a cross-section diagram schematically illustrating a configuration of a microscope section of the microscope apparatus illustrated in FIG. 1. FIG. 3 is a diagram schematically illustrating a configuration of a tilting section of the microscope apparatus illustrated in FIG. 1. FIG. 4 is a cross-section diagram schematically illustrating the state of the A-A cross-section of a tilt driving mechanism included in the tilting section illustrated in FIG. 3. FIG. 5 is a cross-section diagram schematically illustrating the state of the B-B cross-section of the tilt driving mechanism illustrated in FIG. 4.

Referring to FIG. 1, the microscope apparatus 10 according to the first embodiment is provided with a microscope section 110 for performing magnified observation of a subject's eye, an arm section 120 (holding section 120) that holds the microscope section 110, a tilting section 150 provided between the microscope section 110 and the holding section 120 that causes the microscope section 110 to operate such that the illumination optical axis and the observation optical axis tilt treating the approximate center of the interior of the subject's eye as a base point (hereinafter also called the tilt reference point), a base section 130 connected to the base end of the holding section 120 that supports the microscope section 110 and the holding section 120, and a footswitch 140 for inputting various instructions into the microscope apparatus 10.

Note that in the following description, the vertical direction with respect to the horizontal plane (that is, the floor on which the microscope apparatus 10 is installed) is defined to be the z-axis direction. The z-axis direction is also called the up-and-down direction. Also, the direction which is orthogonal to the z-axis direction and in which the holding section 120 extends from the base section 130 is defined to be the x-axis direction. The x-axis direction is also called the forward-and-backward direction. Also, the direction orthogonal to both the x-axis direction and the z-axis direction is defined to be the y-axis direction. The y-axis direction is also called the left-and-right direction. Additionally, a plane parallel to the x-y plane is also called the horizontal plane.

(Base Section)

The base section 130 includes a platform having a planar shape, and multiple casters provided on the bottom face of the platform. One end of the holding section 120 is connected to the top face of the platform, while the microscope section 110 is connected to the side of the other end of the holding section 120 extending from the platform (the front end). Also, the microscope apparatus 10 is in contact with the floor through the casters, and is configured to be movable across the floor by the casters.

(Microscope Section)

The microscope section 110 includes a microscope body for performing magnified observation of a subject's eye. As illustrated in FIG. 2, in the microscope section 110, a light source 112, an illumination optical system 113 that guides light from the light source 112 to the outside as illuminating light for a subject's eye 503, and an observation optical system 114 that guides reflected light (observation light) from the subject's eye 503 to an eyepiece 115 are installed inside a housing 111.

An opening is provided in the bottom end of the housing 111, and an objective lens 116 is fitted into the opening. During observation, the microscope section 110 is disposed directly above the subject's eye 503 such that the objective lens 116 opposes the subject's eye 503.

One or multiple optical elements (such as a lens, a mirror, or a prism) are provided in the illumination optical system 113 (in the illustrated example, the illumination optical system 113 includes multiple lenses). The illumination optical system 113 is designed appropriately such that light from the light source 112 may pass through the objective lens 116 in a direction substantially parallel to the optical axis of the objective lens 116 and irradiate the subject's eye 503.

Reflected light (that is, observation light) from the subject's eye 503 passes through the objective lens 116 and enters the housing ill. One or multiple optical elements (such as a lens, a mirror, or a prism) are provided in the observation optical system 114 (in the illustrated example, the observation optical system 114 includes multiple lenses and a prism). Near the top end of the housing 111, the eyepiece 115 through which the surgeon (in FIG. 2, only a surgeon's eye 501 is illustrated for the sake of convenience) performs magnified observation of the subject's eye 503 is provided, and the observation optical system 114 is designed appropriately such that observation light may be guided to the eyepiece 115. Note that the observation optical system 114 includes a focus lens for focusing and a zoom lens for adjusting the magnification, and during observation, the positions of the focus lens and the zoom lens may be adjusted appropriately such that an image of the subject's eye 503 magnified by a predetermined magnification with the subject's eye 503 in a focused state may be observed.

Also, the optical systems inside the microscope section 110 are designed such that the illumination optical axis and the observation optical axis are substantially coaxial. In the case of the illustrated example, a prism 117 is provided at the position where the optical path of light from the light source 112 passing through the illumination optical system 113 and the optical path of observation light incident on the observation optical system 114 intersect, and the microscope section 110 is configured such that optical axes of the two become substantially the same (for the sake of explanation, in FIG. 2, the arrow indicating the illumination optical axis and the arrow indicating the observation optical axis are intentionally illustrated offset from each other, but in actuality, these optical axes are substantially aligned). As also described in Patent Literature 2 above, a smaller relative angle between the illumination optical axis and the observation optical axis is said to be more preferable to obtain a favorable red reflex and observe the crystalline lens clearly. Consequently, in the present embodiment, configuring the microscope section 110 such that the illumination optical axis and the observation optical axis are substantially coaxial makes it possible to obtain a more favorable red reflex.

Note that the configuration of the microscope section 110 is not limited to the illustrated example. The microscope section 110 may have a configuration similar to any of various known types of optical microscope sections (however, as described above, the microscope section 110 preferably is configured such that the illumination optical axis and the observation optical axis are substantially coaxial). For example, the configurations of the illumination optical system 113 and the observation optical system 114 are not limited to the illustrated example, and these optical systems preferably are configured appropriately to be able to exhibit the desired optical characteristics.

(Holding Section)

The holding section 120 includes multiple rotation axis sections (a first rotation axis section 124 and a second rotation axis section 125) and multiple links (a first arm 121, a second arm 122, and a third arm 123) rotatably joined to each other by the multiple rotation axis sections. Herein, a rotation axis section is used for convenience as a collective term for a member that forms a rotation axis. For example, a rotation axis section may include a bearing, a shaft rotatably inserted into the bearing, a brake that restrains rotation about the rotation axis, and the like.

On the top face of the base section 130, the base end of the first arm 121 that extends in the vertical direction is connected. On the front end of the first arm 121, the base end of the second arm 122 is connected through the first rotation axis section 124 that treats the z-axis direction as the rotation axis direction. In other words, the first arm 121 rotatably supports the second arm 122 through the first rotation axis section 124 treating the z-axis direction as the rotation axis direction. Hereinafter, the rotation axis of the first rotation axis section 124 will also be designed the first axis $O_1$.

The second arm 122 is approximately L-shaped, with the end on the short side connected to the front end of the first arm 121 through the first rotation axis section 124. Consequently, the long side of the approximate L-shape of the second arm 122 extends substantially horizontally. On the end of the long side of the second arm 122 (that is, the front end of the second arm 122), the base end of the third arm 123 is connected through the second rotation axis section 125 that treats the y-axis direction as the rotation axis direction. In other words, the second arm 122 rotatably supports the third arm 123 through the second rotation axis section 125 treating the y-axis direction as the rotation axis direction. Hereinafter, the rotation axis of the second rotation axis section 125 will also be designed the second axis $O_2$.

The third arm 123 extends in the horizontal direction, and on the front end thereof, the microscope section 110 is connected through the tilting section 150, By having the configuration described above, in the holding section 120, by causing the configuration farther on the front end side than the first rotation axis section 124 to rotate about the first rotation axis section 124, the position in the horizontal plane of the microscope section 110 can be decided. Also, by causing the configuration farther on the front end side than the second rotation axis section 125 to rotate about the second rotation axis section 125, the position in the vertical direction of the microscope section 110 can be decided. In this way, in the microscope apparatus 10, by appropriately changing the attitude of the holding section 120 by the rotation of the first rotation axis section 124 and the second rotation axis section 125, the three-dimensional position of the microscope section 110 can be adjusted.

Note that the operations of the first rotation axis section 124 and the second rotation axis section 125 in the holding section 120 may be performed manually or electrically by providing actuators (such as a motor and a control circuit that drives the motor, for example) in these rotation axis sections. In the case in which the operations of the first rotation axis section 124 and the second rotation axis section 125 are performed electrically, the operations preferably are executed in accordance with instruction input by the surgeon through the footswitch 140.

Note that the configuration of the holding section 120 is not limited to the illustrated example. In the first embodiment, the holding section 120 may be configured in any way insofar as the three-dimensional position of the microscope section 110 is adjustable. For example, as one example of another configuration, the holding section 120 may be configured to have six degrees of freedom in the movement of the microscope section 110. According to such a configuration, since it becomes possible to move the microscope section 110 freely in the movable range of the holding section 120, the microscope section 110 can be moved more smoothly to a position corresponding to the subject's eye 503, and convenience for the surgeon can be improved.

(Footswitch)

The footswitch 140 is an input apparatus for performing various types of instruction input with respect to the microscope apparatus 10. The footswitch 140 is provided with multiple seesaw switches and a joystick. For example, by instruction input via the multiple seesaw switches, control of the focusing and magnification of the microscope section 110 may be executed. Also, for example, by instruction input via the joystick, the tilt direction and tilt amount of the microscope section 110 by the tilting section 150 may be controlled.

Note that the control of the movement of the microscope apparatus 10 according to instruction input through the footswitch 140 is not limited to such an example, and in the footswitch 140, any of various types of instruction input performed in a typical microscope apparatus may be performed. Additionally, the microscope apparatus 10 may also be provided with another input apparatus other than the footswitch 140 (such as a switch, a lever, or a touch panel, for example), and any of various types of instruction input that may be performed in a typical microscope apparatus may be performed through the input apparatus.

(Tilting Section)

The tilting section 150 causes the microscope section 110 to move such that the illumination optical axis and the observation optical axis tilt, treating the approximate center of the interior of the subject's eye 503 as a tilt reference point. In other words, the tilting section 150 is a mechanism that, by causing the microscope section 110 to tilt, changes the angle of the illumination optical axis and the observation optical axis with respect to the subject's eye 503.

As described above, during surgery, the subject's eye 503 moves in some cases due to the patient's own movement or treatment operations by the surgeon. At this time, since the patient's head is immobilized, the movements of the subject's eye 503 are movements that tilt the eye axis. In this case, since the relative angle between the eye axis of the subject's eye 503 and the illumination optical axis as well as the relative angle between the eye axis of the subject's eye 503 and the observation optical axis change, there is a risk of no longer obtaining a favorable red reflex.

In the present embodiment, in the case in which such movements of the subject's eye 503 occur, the microscope section 110 is tilted by the tilting section 150 in the direction of the movement. At this time, as described above, the tilting section 150 tilts the microscope section 110 such that the illumination optical axis and the observation optical axis tilt, treating the approximate center of the interior of the subject's eye 503 as a tilt reference point. Consequently, in the case of tilting the microscope section 110 by the tilting section 150 according to the movement of the subject's eye 503, by the tilted microscope section 110, illuminating light is incident on the subject's eye 503 from substantially the front, while in addition, reflected light (that is, observation light) from the fundus is obtained in a state of being observed substantially in front of the subject's eye 503 (in other words, the eye axis of the subject's eye 503 and the illumination optical axis are substantially aligned, while in addition, the eye axis of the subject's eye 503 and the observation optical axis are substantially aligned). In other words, by the tilted microscope section 110, a favorable red reflex can be obtained. Therefore, it becomes possible to continue clear observation of the crystalline lens using the red reflex more smoothly, without performing the troublesome work of adjusting the position and attitude of the microscope section 110.

Hereinafter, FIGS. 3 to 5 will be referenced to describe the configuration of the tilting section 150 in detail. Note that herein, for the sake of simplicity herein, the configuration of the tilting section 150 will be described by taking an example of a case in which the optical axis (that is, the illumination optical axis and the observation optical axis) of the microscope section 110 faces substantially in the vertical direction, as illustrated in FIGS. 3 to 5. It should be noted that in actuality, depending on the attitude of the holding section 120 described above and the movement of the tilting section 150 described later, the extension directions of a first support arm 166, a second support arm 186, and a third support arm 176 may vary from the vertical direction.

FIG. 3 illustrates an enlarged view of the tilting section 150 and microscope section 110 portion illustrated in FIG. 1. As illustrated in FIG. 3, the tilting section 150 includes a first rotation driving mechanism 170, a tilt driving mechanism 180, and a second rotation driving mechanism 160. Between the base end of the microscope section 110 and the front end of the holding section 120, proceeding from down to up in a substantially vertical direction, the first rotation driving mechanism 170, the tilt driving mechanism 180, and the second rotation driving mechanism 160 are disposed in order.

For the sake of explanation, FIG. 3 illustrates the interior configuration of the first rotation driving mechanism 170 and the second rotation driving mechanism 160 by taking a cross-section of housings 171 and 161 described later parallel to the x-z plane (the configuration of the tilt driving mechanism 180 will be described later).

Referring to FIG. 3, the second rotation driving mechanism 160 includes a housing 161, a first gear 162, a second gear 163, a motor 164, a control circuit 165, and a first support arm 166. The first gear 162, the second gear 163, the motor 164, and the control circuit 165 are installed inside the housing 161. Also, the first support arm 166 is installed to extend in a substantially vertical direction facing downward from the housing 161. The front end of the first support arm 166 is securely connected to the top face of a housing 181 of the tilt driving mechanism 180 described later.

The first gear 162 is installed inside the housing 161 such that its rotation axis is substantially parallel to the z-axis direction. The base end of the first support arm 166 is securely connected to the center of the first gear 162. The first support arm 166 is installed to extend downward through an opening provided in the bottom face the housing 161. As the first gear 162 rotates, the first support arm 166 rotates treating its extension direction (that is, a substantially vertical direction) as the rotation axis.

The second gear 163 is installed to engage with the first gear 162. The drive shaft of the motor 164 is securely connected to the center of the second gear 163. By driving the motor 164, the second gear 163 rotates, and the first support arm 166 also rotates through the first gear 162. The type of the motor 164 is not limited, and any of various types of motors may be used. However, as above, since the first support arm 166 rotates in association with the driving of the motor 164, to precisely control the rotational angle of the first support arm 166, it is preferable to use a motor capable of precisely controlling the rotational angle of the drive shaft, like a stepping motor for example, as the motor 164.

The control circuit 165 controls the driving of the motor 164. The control circuit 165 includes a processor such as a central processing unit (CPU) and a storage element such as memory mounted on a board, for example. In the first embodiment, the control circuit 165 drives the motor 164 and causes the first support arm 166 to rotate according to instruction input by the surgeon through the footswitch 140. Specifically, in the case in which the subject's eye 503 moves, the surgeon is able to input an instruction to tilt the microscope section 110 through the footswitch 140. The control circuit 165 cooperates with a control circuit 185 of the tilt driving mechanism 180 described later to drive the motor 164 causing the first support arm 166 to rotate such that the microscope section 110 may tilt in a direction and angle corresponding to the instruction input of the surgeon (details about the driving method of the motor 164 will be described later in (1-2. Operations of microscope apparatus) below).

In this way, the second rotation driving mechanism 160 includes a function of causing the first support arm 166 to rotate treating its extension direction as the rotation axis direction, according to the instruction input of the surgeon. As described above, since the front end of the first support arm 166 is securely connected to the top face of the housing 181 of the tilt driving mechanism 180, by the first support arm 166 rotating in this way, the entire configuration farther on the front end side than the first support arm 166 (the first support arm 166, the tilt driving mechanism 180, the first rotation driving mechanism 170, and the microscope section 110) rotates in a unified manner treating the extension direction of the first support arm 166 as the rotation axis direction.

The first rotation driving mechanism 170 includes a housing 171, a first gear 172, a second gear 173, a motor 174, a control circuit 175, and a third support arm 176. The first gear 172, the second gear 173, the motor 174, and the control circuit 175 are installed inside the housing 171. Also, the third support arm 176 is installed to extend in a substantially vertical direction facing downward from the housing 171. The front end of the third support arm 176 is securely connected to the top face of a housing 111 of the microscope section 110. At this time, the third support arm 176 is disposed on an extension line of the optical axis of the microscope section 110 to be positioned substantially parallel to the optical axis.

The first gear 172 is installed inside the housing 171 such that its rotation axis is substantially parallel to the z-axis direction. The base end of the third support arm 176 is securely connected to the center of the first gear 172. The third support arm 176 is installed to extend downward through an opening provided in the bottom face of the housing 171. As the first gear 172 rotates, the third support arm 176 rotates treating its extension direction (that is, a substantially vertical direction) as the rotation axis.

The second gear 173 is installed to engage with the first gear 172. The drive shaft of the motor 174 is securely connected to the center of the second gear 173. By driving the motor 174, the second gear 173 rotates, and the third support arm 176 also rotates through the first gear 172. The type of the motor 174 is not limited, and any of various types of motors may be used. However, as above, since the third support arm 176 rotates in association with the driving of the motor 174, to precisely control the rotational angle of the third support arm 176, it is preferable to use a motor capable of precisely controlling the rotational angle of the drive shaft, like a stepping motor for example, as the motor 174.

The control circuit 175 controls the driving of the motor 174. The control circuit 175 includes a processor such as a CPU and a storage element such as memory mounted on a board, for example. In the first embodiment, the control circuit 175 drives the motor 174 and causes the third support arm 176 to rotate according to operation input by the surgeon through the footswitch 140. Specifically, as described above, in the case in which the subject's eye 503 moves, the surgeon is able to input an instruction to tilt the microscope section 110 through the footswitch 140. The control circuit 175 cooperates with the control circuit 165 of the second rotation driving mechanism 160 described above to drive the motor 174 such that the third support arm 176 rotates in a direction and angle corresponding to the instruction input of the surgeon. Details about the driving method of the motor 174 will be described later in (1-2. Operations of microscope apparatus) below.

In this way, the first rotation driving mechanism 170 includes a function of causing the third support arm 176 to rotate treating its extension direction as the rotation axis direction, according to the instruction input of the surgeon. As described above, since the front end of the third support arm 176 is securely connected to the top face of the housing 111 of the microscope section 110, by the third support arm 176 rotating in this way, the entire configuration farther on the front end side than the third support arm 176 (the third support arm 176 and the microscope section 110) rotates in a unified manner treating the extension direction of the third support arm 176 (this is a direction substantially aligned with the illumination optical axis and the observation optical axis of the microscope section 110) as the rotation axis direction.

Referring to FIG. 4, the tilt driving mechanism 180 includes a housing 181, a rack 182, a pinion 183, a motor 184, a control circuit 185, and a second support arm 186. The rack 182, the pinion 183, the motor 184, and the control circuit 185 are installed inside the housing 181. Also, the second support arm 186 is installed to extend in a substantially vertical direction facing downward from the housing 181. The front end of the second support arm 186 is securely connected to the top face of the housing 171 of the first rotation driving mechanism 170.

The rack 182 is installed inside the housing 181 such that its extension direction is parallel to the horizontal direction. In the illustrated example, the rack 182 is installed such that its extension direction is parallel to the x-axis direction. Also, the rack 182 is installed inside the housing 181 to be able to move in the rotation axis direction (the direction of the arrow P in the drawing).

The pinion 183 is installed to engage with the rack 182. The drive shaft of the motor 184 is securely connected to the center of the pinion 183. By driving the motor 184, the pinion 183 rotates, thereby causing the rack 182 to move in the direction of the arrow P.

The type of the motor 184 is not limited, and any of various types of motors may be used as the motor 184. However, as described later, since the second support arm 186 also moves in association with the movement in the direction of the arrow P of the rack 182, to precisely control the movement amount of the second support arm 186, it is preferable to use a motor capable of precisely controlling the rotational angle of the drive shaft, like a stepping motor for example, as the motor 184.

The control circuit 185 controls the driving of the motor 184. The control circuit 185 includes a processor such as a CPU and a storage element such as memory mounted on a board, for example. In the first embodiment, the control circuit 185 drives the motor 184 and causes the second support arm 186 to move according to operation input by the surgeon through the footswitch 140. Specifically, as described above, in the case in which the subject's eye 503 moves, the surgeon is able to input an instruction to tilt the microscope section 110 through the footswitch 140. The control circuit 185 drives the motor 184 and causes the second support arm 186 to move such that the microscope section 110 tilts in a direction and angle corresponding to the instruction input of the surgeon. Details about the driving method of the motor 184 will be described later in (1-2. Operations of microscope apparatus) below.

The housing 181 is substantially rectangular, and on the side face whose inner wall opposes the rack 182, an upwardly convex arc-shaped opening 187 is formed. The arc-shaped opening 187 is formed such that the arc has a radius centered on the approximate center of the interior of the subject's eye 503.

The second support arm 186 is installed at a position opposing the outer wall of the side face in which the arc-shaped opening 187 is formed. On the face opposing the side wall of the housing 181 of the second support arm 186, a pin 188 projecting out toward the housing 181 is formed, and the pin 188 is inserted into the arc-shaped opening 187 and into the interior of the housing 181. On the face of the rack 182 opposing the side wall where the arc-shaped opening 187 of the housing 181 is formed, a long groove 189 that is longitudinal in the vertical direction is formed, and the front end of the pin 188 of the second support arm 186 is engaged with the long groove 189 (see also FIG. 5). Consequently, when the rack 182 moves in the direction of the arrow P, the second support arm 186 connected to the rack 182 through an engaging section 188*b* of the pin 188 engaging with the long groove 189 also moves together in the direction of the arrow P.

Herein, as illustrated in FIG. 5, the cross-sectional shape in the x-y plane of the engaging section 188*b* of the pin 188 engaging with the long groove 189 is a circle having a diameter that is substantially the same as the length in the x-axis direction of the long groove 189, and the pin 188 is rotatably engaged with the long groove 189. Also, as illustrated in FIG. 5, the cross-sectional shape in the x-y plane of an engaging section 188*a* of the pin 188 engaging with the arc-shaped opening 187 is formed to have the same shape as the shape of the region where the long groove 189 and the arc-shaped opening 187 overlap when the arc-shaped opening 187 is projected onto the long groove 189. In other words, the cross-sectional shape of the engaging section 188*a* of the pin 188 engaging with the long groove 189 has substantially the same shape as a part of the arc-shaped opening 187 (specifically, the portion obtained by cutting off the arc-shaped opening 187 along two straight lines parallel to the vertical direction). Consequently, the pin 188 is able to move along the arc-shaped opening 187 inside the arc-shaped opening 187, but is unable to rotate inside the arc-shaped opening 187.

According to such a configuration, when the pin 188 engaged with the long groove 189 moves in the same direction in association with movement in the direction of the arrow P of the rack 182, the pin 188 moves vertically inside the long groove 189 while also moving along the arc-shaped opening 187. In other words, in the state illustrated in FIG. 5 for example, in the case in which the rack 182 moves to the right in the drawing, the pin 188 moves to the right along the arc-shaped opening 187. The second support arm 186 on which the pin 188 is formed also moves along the arc-shaped opening 187.

In addition, at this point, as described above, since the cross-section of the engaging section 188*a* of the pin 188 engaging with the arc-shaped opening 187 has substantially the same shape as a part of the arc-shaped opening 187, and the pin 188 is unable to rotate inside the arc-shaped opening 187, the pin 188 moves while inclining according to the curvature of the arc-shaped opening 187. In other words, the pin 188 moves along the arc-shaped opening 187 while inclining such that the straight line passing through the midpoint on the top edge and the midpoint on the bottom edge of the cross-section of the engaging section 188*a* of the pin 188 engaging with the arc-shaped opening 187 (this is in other words a straight line substantially parallel to the extension direction of the second support arm 186) always points toward the center of the arc of the arc-shaped opening 187. As described above, since the arc-shaped opening 187 is formed such that the arc has a radius centered on the approximate center of the interior of the subject's eye 503, ultimately, in the case in which the pin 188 moves along the arc-shaped opening 187, the second support arm 186 may move such that the front end of the second support arm 186 always points towards the approximate center of the interior of the subject's eye 503 and also in a state of maintaining a substantially constant distance to the approximate center of the interior of the subject's eye 503.

As described above, since the front end of the second support arm 186 is securely connected to the top face of the housing 171 of the first rotation driving mechanism 170, by having the second support arm 186 move while tilting along the arc-shaped opening 187 in this way, the entire configuration farther on the front end side than the second support arm 186 (that is, the second support arm 186, the first rotation driving mechanism 170, and the microscope section 110) tilts treating the approximate center of the interior of the subject's eye 503 as a base point. In this way, the tilt driving mechanism 180 includes a function of tilting the microscope section 110 along the extension direction of the arc-shaped opening 187 in a state of the optical axis of the microscope section 110 pointing towards the approximate center of the interior of the subject's eye 503 and also in a state of maintaining a substantially constant distance between the microscope section 110 and the approximate center of the interior of the subject's eye 503.

The above describes the configuration of the tilting section 150. By having the configuration described above, in the tilting section 150, it becomes possible to tilt the microscope section 110 in any direction treating the approximate center of the interior of the subject's eye 503 as a tilt reference point. Specifically, by having the configuration farther on the front end side than the first support arm 166 rotate by the second rotation driving mechanism 160, the extension direction of the arc-shaped opening 187 in the tilt driving mechanism 180, that is, the tilt direction of the microscope section 110, may be adjusted in any direction in the horizontal plane. In other words, by appropriately controlling the driving of the second rotation driving mechanism 160 and the tilt driving mechanism 180, the microscope section 110 may be tilted in any direction treating the approximate center of the interior of the subject's eye 503 as the tilt reference point.

However, at this time, if the configuration farther on the front end side than the first support arm 166 is rotated by the second rotation driving mechanism 160, the microscope section 110 will also rotate simultaneously, and therefore there is a possibility that the eyepiece 115 will no longer point in the direction of the surgeon. In this case, by causing the configuration farther on the front end side than the third support arm 176 to rotate by the first rotation driving mechanism 170, it is possible to adjust the direction of the eyepiece 115 of the microscope section 110.

Hereinafter, operations of the tilting section 150 will be described in detail.

(1-2. Operations of Microscope Apparatus)

Operations of the microscope apparatus 10 described above, and particularly operations of the tilting section 150, will be described.

When performing surgery, the casters of the base section 130 are used to move the microscope apparatus 10 close to the operating table. Additionally, the attitude of the holding section 120 is changed appropriately, and the position and attitude of the microscope section 110 are adjusted such that an eye of the patient lying on the operating table (the subject's eye 503) is observable. Specifically, the position and attitude of the microscope section 110 are adjusted such that the eye axis of the subject's eye 503 is substantially aligned with the illumination optical axis and the observation optical axis, such that a favorable red reflex is obtained. At this point, an operation of tilting the microscope section 110 by the tilting section 150 may also be used together to adjust the position and attitude of the microscope section 110.

Suppose that surgery is started, and partway through, the subject's eye 503 moves and the red reflex is lost. In this case, the surgeon inputs, through the footswitch 140, instruction input for tilting the microscope section 110 by a desired angle in the direction that the subject's eye 503 moved such that a favorable red reflex is obtained. The method of instruction input may be any method. For example, while a joystick of the footswitch 140 is inclined, the microscope section 110 may move to tilt in the inclined direction. In this case, it is sufficient for the surgeon to operate the joystick while observing the subject's eye 503 with the microscope section 110, until a favorable red reflex is obtained.

The tilting section 150 receiving the instruction input tilts the microscope section 110 in a direction corresponding to the instruction input and by an amount corresponding to the instruction input. Herein, given the structure of the tilt driving mechanism 180, the tilting of the microscope section 110 by the tilt driving mechanism 180 is limited to a single plane parallel to the movement direction of the rack 182 as indicated by the arrow P (that is, the extension direction of the arc-shaped opening 187). In actuality, since the subject's eye 503 tilts in all directions, it is not possible to tilt the microscope section 110 in the direction that the subject's eye 503 has moved with only operations of the microscope section 110 by the tilt driving mechanism 180. In contrast, if the configuration farther on the front end side than the first support arm 166 (the first support arm 166, the tilt driving mechanism 180, the first rotation driving mechanism 170, and the microscope section 110) is made to rotate by the second rotation driving mechanism 160, it becomes possible to adjust the direction in which the microscope section 110 is tilted in any way by the tilt driving mechanism 180. In this way, in the first embodiment, by appropriately combining the rotation and movement of the microscope section 110 by the second rotation driving mechanism 160 and the tilt driving mechanism 180, it becomes possible to tilt the microscope section 110 in any direction.

Specifically, the control circuit 165 of the second rotation driving mechanism 160 receiving instruction input from the surgeon drives the motor 164 and causes the configuration farther on the front end side than the first support arm 166 to rotate by a suitable amount such that the extension direction of the arc-shaped opening 187 of the tilt driving mechanism 180 points in a tilt direction corresponding to the instruction input. Also, at the same time, the control circuit 185 of the tilt driving mechanism 180 drives the motor 184 and tilts the microscope section 110 towards the extension direction of the arc-shaped opening 187 by an amount corresponding to the instruction input. In this way, by having the second rotation driving mechanism 160 and the tilt driving mechanism 180 work together, the microscope section 110 may be tilted according to the instruction input from the surgeon.

Also, at this time, in the first embodiment, the control circuit 175 of the first rotation driving mechanism 170 drives the motor 174 and causes the configuration farther on the front end side than the third support arm 176 (the third support arm 176 and the microscope section 110) to rotate in the reverse direction of the direction of rotation by the second rotation driving mechanism 160 by an amount equal to the rotation by the second rotation driving mechanism 160. At this point, when the microscope section 110 is tilted, if the microscope section 110 is rotated by the second rotation driving mechanism 160, there is a risk that the microscope section 110 will be tilted in a state in which the eyepiece 115 of the microscope section 110 is not pointing at the surgeon. In contrast, by causing the microscope section 110 to rotate by the first rotation driving mechanism 170 to cancel out the rotation of the microscope section 110 by the second rotation driving mechanism 160 so to speak, the microscope section 110 is tilted in a state in which the eyepiece 115 is always pointing at the surgeon, thereby making it possible to solve the inexpedience of the direction of the eyepiece 115 changing due to the tilting operation.

If the microscope section 110 is tilted by a desired angle such that a favorable red reflex is obtained, the surgeon is able to continue surgery as-is.

The above describes operations of the microscope apparatus 10. As described above, in the first embodiment, the operation of tilting the microscope section 110 is executed by the first rotation driving mechanism 170, the second rotation driving mechanism 160, and the tilt driving mechanism 180. In the operation of tilting the microscope section 110, given the structure of the tilt driving mechanism 180, the microscope section 110 is tilted treating the approximate center of the interior of the subject's eye 503 as the tilt reference point. In other words, the state after tilting is a state in which the illumination optical axis and the observation optical axis are pointing at the approximate center of the interior of the subject's eye 503 and also a state in which the distance between the microscope section 110 and the approximate center of the subject's eye 503 is substantially unchanged. In other words, at the position and attitude of the microscope section 110 after tilting, a favorable red reflex is already obtained. Consequently, when tilting the microscope section 110, it is not necessary make fine adjustments to the position and attitude to obtain a favorable red reflex. In other words, it is sufficient for the surgeon to specify just the direction in which to tilt and the tilt angle with a simple operation through the footswitch 140, making it possible to execute the operation of tilting the microscope section 110 smoothly according to the motion of the subject's eye 503 such that a favorable red reflex is obtained, without performing a complicated operation. Also, during the tilting operation, since the eyepiece 115 of the microscope section 110 is always in a state of pointing at the surgeon due to the first rotation driving mechanism 170, the work of adjusting the position of the eyepiece 115 is also saved. Consequently, according to the first embodiment, smoother surgery may be achieved.

(1-3. Functional Configuration)

Figure 6:
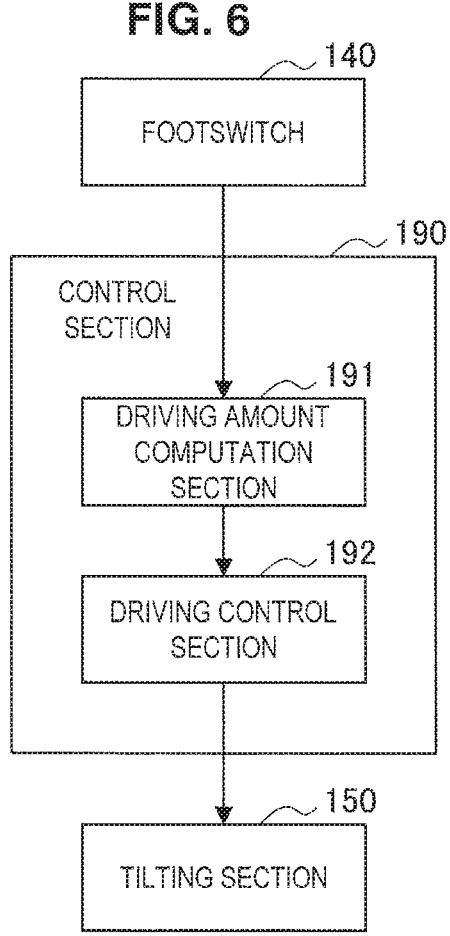
FIG. 6 is a function block diagram illustrating one example of a functional configuration of a control section related to an operation of tilting the microscope section according to the first embodiment.

A functional configuration of the control section that executes control related to the operation of tilting the microscope section 110 in the microscope apparatus 10 described above will be described. FIG. 6 is a function block diagram illustrating one example of a functional configuration of a control section related to an operation of tilting the microscope section 110 according to the first embodiment.

Referring to FIG. 6, the control section 190 related to the operation of tilting the microscope section 110 functionally includes a driving amount computation section 191 and a driving control section 192. Herein, the control section 190 conceptually illustrates the functions of the control circuit 175 of the first rotation driving mechanism 170, the control circuit 165 of the second rotation driving mechanism 160, and the control circuit 185 of the tilt driving mechanism 180 described with reference to FIGS. 1 to 5 as a single block. By having at least one of these control circuits 165, 175, and 185 execute computational processing in accordance with a predetermined program, each of the above functions (the driving amount computation section 191 and the driving control section 192) in the control section 190 may be realized.

In FIG. 6, blocks representing the footswitch 140 and the tilting section 150 are illustrated as well for the sake of explanation. When the operation of tilting the microscope section 110 is performed, instruction input by the surgeon is performed through the footswitch 140. The instruction input at least includes information about the direction in which to tilt and the amount by which to tilt the microscope section 110.

The instruction input is input into the driving amount computation section 191 of the control section 190. The driving amount computation section 191 computes a driving amount in the tilting section 150 on the basis of the information about the direction in which to tilt and the amount by which to tilt the microscope section 110 included in the instruction input. Specifically, on the basis of the information about the direction in which to tilt the microscope section 110, the driving amount computation section 191 computes a rotation amount of the first support arm 166 of the second rotation driving mechanism 160 to align the tilt direction of the microscope section 110 by the tilt driving mechanism 180 with the direction. Additionally, the driving amount computation section 191 takes into account the gear ratio of the first gear 162 and the second gear 163 of the second rotation driving mechanism 160 and the like to compute a driving amount (rotation amount) of the motor 164 to achieve the above rotation amount of the first support arm 166. In the first embodiment, the driving amount computation section 191 is configured to be able to grasp the current rotational angle of the first support arm 166 with reference to a predetermined position, and the driving amount computation section 191 is able to compute the desired rotation amount of the first support arm 166 on the basis of the grasped current rotational angle of the first support arm 166. For example, a potentiometer may be installed on the drive shaft of the motor 164 of the second rotation driving mechanism 160, and the driving amount computation section 191 may grasp the current rotational angle of the first support arm 166 on the basis of a detection value of the rotational angle of the drive shaft by the potentiometer.

Also, at the same time, on the basis of the information about the amount by which to tilt the microscope section 110, the driving amount computation section 191 takes into account the gear ratio of the rack 182 and the pinion 183 of the tilt driving mechanism 180 and the like to compute a driving amount (rotation amount) of the motor 184 such that the amount by which to tilt is achieved.

Furthermore, the driving amount computation section 191 sets a rotation amount of the same magnitude but of inverse sign (that is, in the opposite direction) compared to the rotation amount of the first support arm 166 by the second rotation driving mechanism 160 as a rotation amount of the third support arm 176 by the first rotation driving mechanism 170. Additionally, the driving amount computation section 191 takes into account the gear ratio of the first gear 172 and the second gear 173 of the first rotation driving mechanism 170 and the like to compute a driving amount (rotation amount) of the motor 174 to achieve the above rotation amount of the third support arm 176.

The driving amount computation section 191 provides information about the computed driving amounts of the motors 164, 174, and 184 to the driving control section 192.

The driving control section 192 controls the driving of the motors 164, 174, and 184 on the basis of the information about the driving amounts of the motors 164, 174, and 184 computed by the driving amount computation section 191. With this arrangement, an operation of tilting the microscope section 110 according to instruction input by the surgeon through the footswitch 140 is executed.

The above describes a functional configuration of the control section 190 that executes control related to the operation of tilting the microscope section 110 in the microscope apparatus 10.

(1-4. Control Method)

Figure 7:
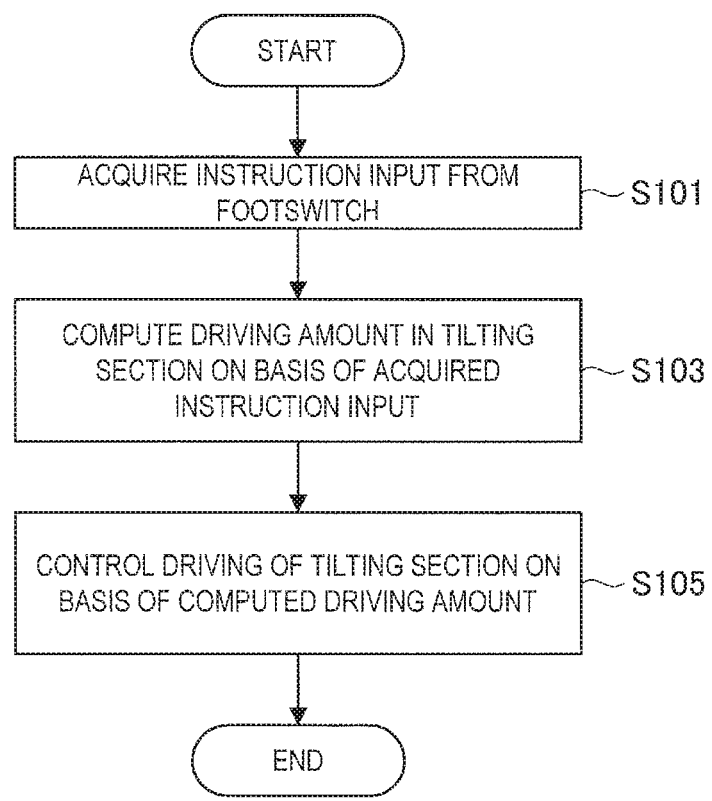
FIG. 7 is a flowchart illustrating an example of a processing procedure of a control method related to the operation of tilting the microscope section according to the first embodiment.

A processing procedure of the control method related to the operation of tilting the microscope section 110 in the microscope apparatus 10 according to the first embodiment performed by the control section 190 described above will be described using a flowchart. FIG. 7 is a flowchart illustrating an example of a processing procedure of a control method related to the operation of tilting the microscope section 110 according to the first embodiment. Note that each process illustrated in FIG. 7 corresponds to each process executed by the control section 190 illustrated in FIG. 6, and by having a processor included in the control section 190 execute computational processing in accordance with a predetermined program, each process illustrated in FIG. 7 may be executed. Since the details of each process illustrated in FIG. 7 have already been described above in the description of the functions of the control section 190, in the following description of the processing procedure of the control method, an overview of each process will be described briefly, and detailed description will be omitted.

Referring to FIG. 7, in the control method related to the operation of tilting the microscope section 110 according to the first embodiment, first, instruction input from the footswitch 140 is acquired (step S101). The process in step S101 corresponds to the process in which instruction input for tilting the microscope section 110, performed by the surgeon through the footswitch 140, is input into the control section 190 as described with reference to FIG. 6.

Next, the driving amount in the tilting section 150 is computed on the basis of the acquired instruction input (step S103). Specifically, in step S103, each of the driving amount of the motor 164 to achieve the rotation amount of the first support arm 166 corresponding to the instruction input in the second rotation driving mechanism 160, the driving amount of the motor 184 to achieve the tilt of the second support arm 186 corresponding to the instruction input in the tilt driving mechanism 180, and the driving amount of the motor 174 to achieve the rotation amount of the third support arm 176 corresponding to the instruction input in the first rotation driving mechanism 170 is computed. The process in step S103 corresponds to the process executed by the driving amount computation section 191 illustrated in FIG. 6.

Next, the driving of the tilting section 150 is controlled on the basis of the computed driving amounts (step S105). Specifically, in step S105, the motors 164, 174, and 184 are driven according to the driving amounts computed in step S103. The process in step S105 corresponds to the process executed by the driving control section 192 illustrated in FIG. 6.

The above describes a processing procedure of the control method related to the operation of tilting the microscope section 110 in the microscope apparatus 10.

(1-5. Modification)

One modification of the first embodiment will be described. In the exemplary configuration described above, the operation of tilting the microscope section 110 is performed in accordance with instruction input of the surgeon through the footswitch 140, that is to say, manually. However, the first embodiment is not limited to such an example. For example, the operation of tilting the microscope section 110 may also be performed automatically. Herein, as one modification of the first embodiment, a modification in which the operation of tilting the microscope section 110 is performed automatically will be described.

The microscope apparatus according to the present modification corresponds to additionally providing the microscope apparatus 10 illustrated in FIGS. 1 to 5 with a brightness detection apparatus that detects the brightness of reflected light from the fundus (retina) of the subject's eye 503. Any of various known types of apparatus that may detect brightness, such as an optical sensor or a camera, may be used as the brightness detection apparatus. Since the rest of the configuration of the microscope apparatus according to the present modification is similar to the microscope apparatus 10 described above, a detailed description is omitted here.

Figure 8:
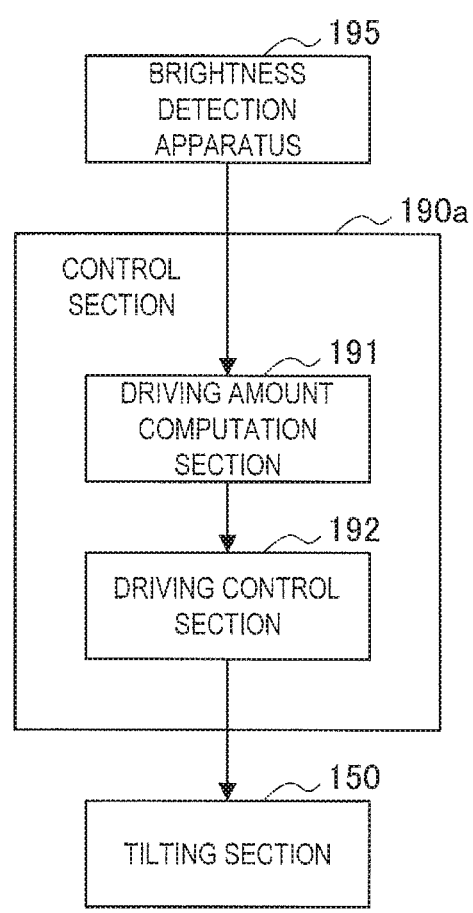
FIG. 8 is a function block diagram illustrating one example of a functional configuration of a control section related to an operation of tilting the microscope section according to one modification of the first embodiment.

FIG. 8 is a function block diagram illustrating one example of a functional configuration of a control section related to an operation of tilting the microscope section 110 according to one modification of the first embodiment. Referring to FIG. 8, the control section 190a related to the operation of tilting the microscope section 110 according to the present modification functionally includes the driving amount computation section 191 and the driving control section 192. Herein, the control section 190a conceptually illustrates the functions of the control circuit 175 of the first rotation driving mechanism 170, the control circuit 165 of the second rotation driving mechanism 160, and the control circuit 185 of the tilt driving mechanism 180 in the microscope apparatus according to the present modification as a single block. By having at least one of these control circuits 165, 175, and 185 execute computational processing in accordance with a predetermined program, each of the above functions (the driving amount computation section 191 and the driving control section 192) in the control section 190a may be realized.

In FIG. 8, blocks representing a brightness detection apparatus 195 and the tilting section 150 are illustrated as well for the sake of explanation. In the present modification, during surgery, the brightness of the reflected light from the fundus of the subject's eye 503 is detected successively at a predetermined interval by the brightness detection apparatus 195. The brightness detection apparatus 195 transmits information about the detected brightness to the driving amount computation section 191 of the control section 190 successively every time the brightness is detected.

The functions of the driving amount computation section 191 and the driving control section 192 are substantially similar to these functions in the exemplary configuration described above illustrated in FIG. 6. In other words, the driving amount computation section 191 computes the driving amount in the tilting section 150, and the driving control section 192 drives the tilting section 150 according to the driving amount computed by the driving amount computation section 191. However, in the present modification, the driving amount computation section 191 and the driving control section 192 tilt the microscope section 110 not based on instruction input by the surgeon, but automatically on the basis of a predetermined algorithm such that the brightness of the reflected light is maximized.

The specific content of the algorithm that drives the microscope section 110 automatically such that the brightness of the reflected light is maximized is not limited, and any of various known types of algorithms may be used as the algorithm. For example, an algorithm may be applied in which, by repeatedly executing a process of computing the driving amounts by the driving amount computation section 191 and a driving control process based on the driving amounts by the driving control section 192 while successively referencing information about the brightness transmitted from the brightness detection apparatus 195, the microscope section 110 is tilted little by little in a direction in which the brightness gradually becomes greater. Alternatively, for example, in the case in which the brightness detection apparatus 195 is a camera, an image (moving image) of the subject's eye taken by the camera may be transmitted to the driving amount computation section 191. In this case, an algorithm may be applied in which the driving amount computation section 191 recognizes the direction in which the subject's eye 503 has moved by analyzing the image, and on the basis of the result, computes an appropriate tilt direction and tilt amount of the microscope section 110 such that the brightness of the reflected light is maximized, or in other words, such that a favorable red reflex is obtained, and computes the driving amounts by the tilting section 150. Otherwise, any of various types of algorithms typically used may be applied.

Figure 9:
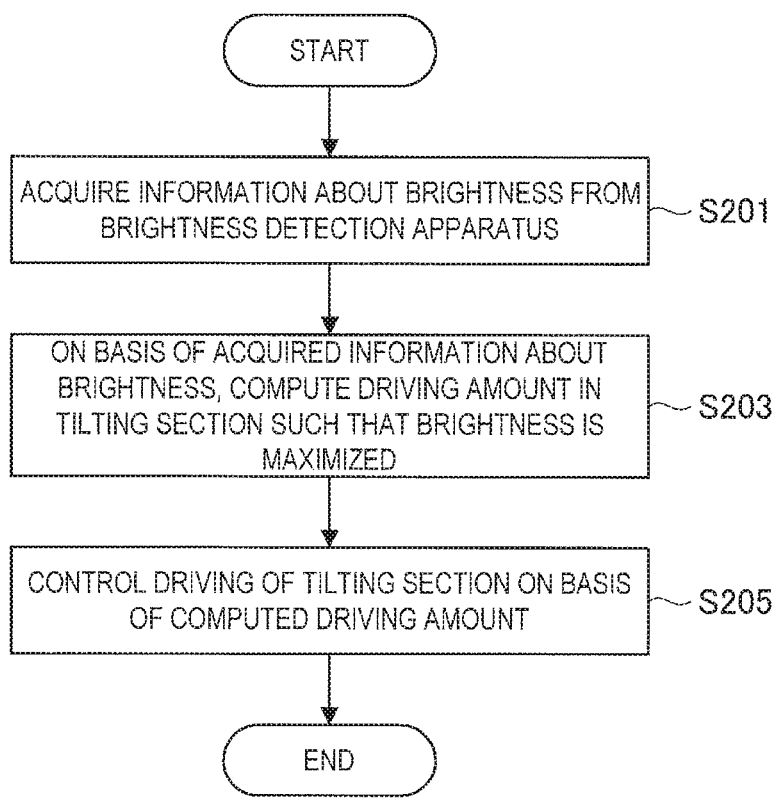
FIG. 9 is a flowchart illustrating an example of a processing procedure of a control method related to the operation of tilting the microscope section according to one modification of the first embodiment.

A processing procedure of the control method related to the operation of tilting the microscope section 110 in the microscope apparatus 110 according to the modification performed by the control section 190a described above will be described using a flowchart. FIG. 9 is a flowchart illustrating an example of a processing procedure of a control method related to the operation of tilting the microscope section 110 according to the modification. Note that each process illustrated in FIG. 9 corresponds to each process executed by the control section 190a illustrated in FIG. 8, and by having a processor included in the control section 190a execute computational processing in accordance with a predetermined program, each process illustrated in FIG. 9 may be executed. Since the details of each process illustrated in FIG. 9 have already been described above in the description of the functions of the control section 190a, in the following description of the processing procedure of the control method, an overview of each process will be described briefly, and detailed description will be omitted.

Referring to FIG. 9, in the control method related to the operation of tilting the microscope section 110 according to the present modification, first, information about the brightness of reflected light from the fundus of the subject's eye 503 is acquired from the brightness detection apparatus 195 (step S201). The process in step S201 corresponds to the process described with reference to FIG. 8, in which information about the brightness detected by the brightness detection apparatus 195 is transmitted to the control section 190a.

Next, on the basis of the acquired information about the brightness, a driving amount in the tilting section 150 that would maximize the brightness is computed (step S203). Specifically, in step S203, the driving amount in the tilting section 150 that would maximize the brightness is computed automatically in accordance with a predetermined algorithm. The process in step S205 corresponds to the process executed by the driving amount computation section 191 illustrated in FIG. 8.

Next, the driving of the tilting section 150 is controlled on the basis of the computed driving amounts (step S205). Specifically, in step S205, the motors 164, 174, and 184 are driven according to the driving amounts computed in step S203. The process in step S205 corresponds to the process executed by the driving control section 192 illustrated in FIG. 8.

The above describes a modification in which the operation of tilting the microscope section 110 is performed automatically.

Note that it is also possible to switch appropriately during surgery between a mode in which the operation of tilting the microscope section 110 described above is performed manually and a mode in which the operation of tilting the microscope section 110 is performed automatically. For example, the microscope apparatus 10 may be provided with a switch that switches between these modes, and these modes may be switched appropriately by instruction input through the switch by the surgeon. For example, in the case in which the operation of tilting the microscope section 110 is performed automatically, the microscope section 110 may move automatically even at a timing unintended by the surgeon, and therefore in some cases, there may be a risk that the motion of the microscope section 110 will interfere with the work of the surgeon. By making it possible to switch appropriately between manual/automatic operation of tilting the microscope section 110 according to instruction input by the surgeon, the surgeon is able to cause the operation of tilting the microscope section 110 to be performed automatically only as needed, and therefore is freed from the irritation of the microscope section 110 moving automatically, and smoother surgery may be achieved.

Also, the switching between manual/automatic operation of tilting the microscope section 110 itself may be performed automatically. For example, on the basis of information about the brightness of reflected light from the retina of the subject's eye 503 detected by the brightness detection apparatus 195, a time during which the brightness is a predetermined threshold value or less (or a time during which the brightness is less than a predetermined threshold value) may be measured, and in the case in which the time exceeds a fixed time (or in the case in which the time is equal to or greater than the fixed time), the operation of tilting the microscope section 110 may be performed automatically.

Such a measurement process and determination process may be executed appropriately by the control section 190a described above for example. By automatically performing the switching between manual/automatic operation of tilting the microscope section 110 itself even without the surgeon performing instruction input related to switching, the work to be performed by the surgeon can be reduced, making it possible to lessen the burden on the surgeon further.

2. Second Embodiment

A second embodiment of the present disclosure will be described. As described above, the microscope apparatus 10 according to the first embodiment is configured to be able to perform an operation of tilting the microscope section 110 treating the approximate center of the interior of the subject's eye 503 as a tilt reference point. According to such a configuration, in a case in which a need occurs to move the microscope section 110 in response to a movement of the subject's eye 503 to obtain a favorable red reflex, by simply tilting the microscope section 110, it becomes possible to continue observation associated with a favorable red reflex immediately, without the need to make fine adjustments to the position and attitude, and smooth surgery may be achieved.

At this point, there exist microscope apparatus configured to be able to execute a pivot operation. A pivot operation refers to an operation of moving the microscope section such that that the optical axis of the microscope section stays pointed at a predetermined point in space (hereinafter called the pivot point). Since a pivot operation makes it possible to observe the same site from a variety of directions, more detailed observation of an affected area becomes possible.

The tilt reference point in the first embodiment may be taken to correspond to the pivot point, and the microscope apparatus 10 according to the first embodiment may be said to be a microscope apparatus capable of a pivot operation in which the pivot point is set to the approximate center of the interior of the subject's eye 503 so to speak. Conversely, in a microscope apparatus configured to be capable of a pivot operation, if the pivot point is set to the approximate center of the interior of the subject's eye 503, it is possible to obtain advantageous effects similar to the microscope apparatus 10 according to the first embodiment.

In this way, in the present disclosure, the configuration of the microscope apparatus is not limited to that of the microscope apparatus 10 according to the first embodiment, and may also be an other configuration insofar as a pivot operation is possible in a stale with the pivot point set to the approximate center of the interior of the subject's eye 503. The second embodiment and the third embodiment described later are embodiments in which the microscope apparatus has such an other configuration.

(2-1. Configuration of Microscope Apparatus)

Figure 10:
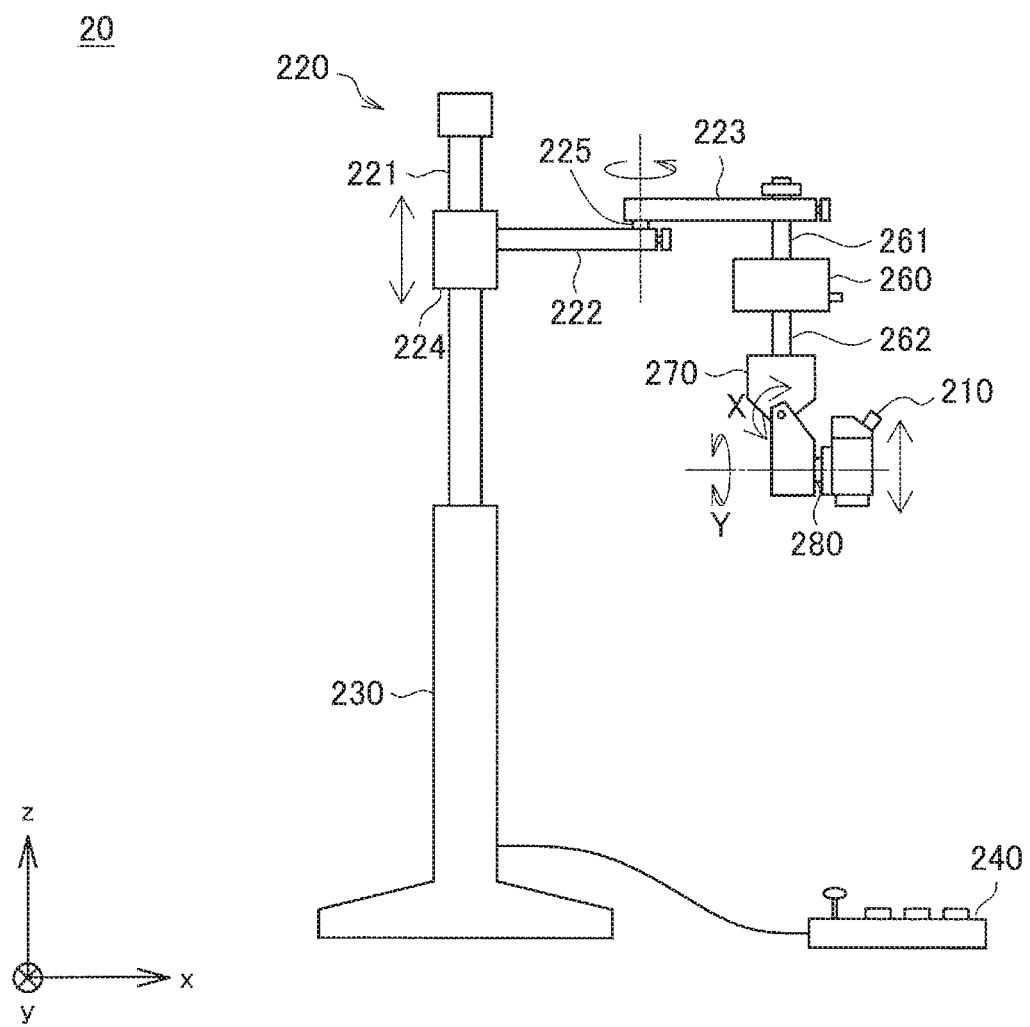
FIG. 10 is a diagram schematically illustrating an overall configuration of a microscope apparatus according to a second embodiment.

FIG. 10 will be referenced to describe a configuration of the microscope apparatus according to the second embodiment of the present disclosure. FIG. 10 is a diagram schematically illustrating an overall configuration of the microscope apparatus according to the second embodiment.

Referring to FIG. 10, the microscope apparatus 20 according to the second embodiment is provided with a microscope section 210 for performing magnified observation of a subject's eye, an arm section 220 (holding section 220) that holds the microscope section 210, an x-y apparatus 260, provided between the holding section 220 and the microscope section 210, that moves the microscope section 210 in the x-y plane, an elevation apparatus 270, provided between the x-y apparatus 260 and the microscope section 210, capable of rotating the microscope section 210 about a rotation axis parallel to the y-axis (that is, in the X direction of the diagram and about a rotation axis parallel to the y-axis (that is, in the Y direction of the diagram), a linear motion mechanism 280, provided between the elevation apparatus 270 and the microscope section 210, capable of moving the microscope section 210 in the z-axis direction, a base section 230 to which the base end of the holding section 220 is connected that supports the microscope section 210 and the holding section 220, and a footswitch 240 for inputting various instructions into the microscope apparatus 20.

The microscope section 210 has a configuration and functions that are substantially the same as the microscope section 110 according to the first embodiment. In other words, the microscope section 210 includes a light source, an illumination optical system, an observation optical system, and an eyepiece, and is configured such that the illumination optical axis and the observation optical axis are substantially coaxial.

The footswitch 240 is an input apparatus for performing various types of instruction input with respect to the microscope apparatus 20. The footswitch 240 is provided with multiple seesaw switches and a joystick. In the second embodiment, the driving of the x-y apparatus 260, the elevation apparatus 270, and the linear motion mechanism 280 can be operated by the footswitch 240. In addition, the driving of a linear motion mechanism 224 and a rotation axis section 225 of the holding section 120 described later may also be performed in accordance with instruction input through the footswitch 240. Also, by instruction input through the joystick, the tilt direction and tilt amount of the microscope section 110 may be controlled (details will be described later in (2-2. Operations of microscope apparatus) below). Otherwise, the footswitch 240 may have similar functions as the footswitch 140 according to the first embodiment described above.

The holding section 220 includes multiple movable sections (the linear motion mechanism 224 and the rotation axis section 225) and multiple links (a first arm 221, a second arm 222, and a third arm 223) joined to each other through these multiple movable sections.

The base section 230 is the base of the microscope apparatus 20, and the arm section 220 extends from the base section 230. The base section 230 has functions that are substantially the same as the base section 130 according to the first embodiment.

The base end of the first arm 221 that extends in the vertical direction is supported by the base section 230. The base end of the second arm 222 is connected to a site near the top end of the first arm 221 through the linear motion mechanism 224. The linear motion mechanism 224 supports the second arm 222 to allow translational movement in the z-axis direction with respect to the first arm 221.

The base end of the second arm 222 is connected to the linear motion mechanism 224 to extend in the horizontal direction, while the front end is connected to the base end of the third arm 223 through the rotation axis section 225 that treats the z-axis direction as the rotation axis direction. In other words, the second arm 222 rotatably supports the third arm 223 through the rotation axis section 225 treating the z-axis direction as the rotation axis direction.

The base end of the third arm 223 is also connected to the rotation axis section 225 to extend in the horizontal direction. In other words, rotation operations about the rotation axis section 225 cause the third arm 223 to turn to the left or right with respect to the second arm 222.

By having the configuration described above, in the holding section 220, by using the linear motion mechanism 224 to translationally move the configuration farther on the front end side than the linear motion mechanism 224, the position in the vertical direction of the microscope section 210 can be adjusted. Also, by causing the configuration farther on the front end side than the rotation axis section 225 to rotate about the rotation axis section 225, the position in the horizontal plane of the microscope section 210 can be adjusted. In this way, in the microscope apparatus 20, by appropriately changing the attitude of the holding section 220 by the linear motion mechanism 224 and the rotation axis section 225, the three-dimensional position of the microscope section 210 can be adjusted. Note that the operations of the linear motion mechanism 224 and the rotation axis section 225 in the holding section 220 may be performed manually or electrically by providing actuators (such as a motor and a control circuit that drives the motor, for example) in these configurations. In the case in which the operations of the linear motion mechanism 224 and the rotation axis section 225 are performed electrically, the operations preferably are executed in accordance with instruction input by the surgeon through the footswitch 240.

The base end of a first support arm 261 that extends downward in the vertical direction is connected to the front end of the third arm 223, and the x-y apparatus 260 is connected to the front end of the first support arm 261. The base end of a second support arm 262 that extends downward in the vertical direction is connected to the x-y apparatus 260, and the x-y apparatus 260 is configured to allow the second support arm 262 to move in the horizontal plane. Inside the x-y apparatus 260, a motor, a control circuit that controls the driving of the motor, a power transmission that converts the rotation of the drive shaft of the motor into movement in the horizontal plane of the second support arm 262, and the like are installed. In the x-y apparatus 260, on the basis of instruction input by the surgeon through the footswitch 240, the control circuit drives the motor and causes the second support arm 262 to move in the horizontal plane to a position corresponding to the instruction input.

The microscope section 210 is connected to the front end of the second support arm 262 through the elevation apparatus 270. The elevation apparatus 270 includes a rotation axis section that rotatably supports the configuration farther on the front end side than itself by treating the y-axis direction as the rotation axis direction (in other words, supports to allow rotation in the X direction of the diagram) and a rotation axis section that rotatably supports the configuration farther on the front end side than itself by treating the x-axis direction as the rotation axis direction (in other words, supports to allow rotation in the Y direction of the diagram), which are disposed in succession. In these rotation axis sections, a motor, a control circuit that controls the driving of the motor, and the like are installed. In these rotation axis sections, on the basis of instruction input by the surgeon through the footswitch 240, the control circuit drives the motor and causes the microscope section 210 to move in the X direction and the Y direction by an amount corresponding to the instruction input.

In this way, in the microscope apparatus 20, the position in the horizontal plane of the microscope section 210 is adjustable by the x-y apparatus 260, and the direction of the optical axis of the microscope section 210 is adjustable by the elevation apparatus 270.

Furthermore, the linear motion mechanism 280 allowing the microscope section 210 to move in the z-axis direction may be provided at the site of connection between the elevation apparatus 270 and the microscope section 210. When a subject's eye is observed by the microscope section 210, the linear motion mechanism 280 is for adjusting the position in the z-axis direction of the microscope section 210 such that the subject's eye is brought into focus.

(2-2. Operations of Microscope Apparatus)

In the microscope apparatus 20 described above, by causing the x-y apparatus 260, the elevation apparatus 270, the linear motion mechanism 224 and/or the linear motion mechanism 280 to operate appropriately, it is possible to perform a pivot operation (that is, an operation of tilting the microscope section 210). In other words, in the second embodiment, a tilting section may be realized by the x-y apparatus 260, the elevation apparatus 270, the linear motion mechanism 224 and/or the linear motion mechanism 280. Hereinafter, the operations of the x-y apparatus 260, the elevation apparatus 270, the linear motion mechanism 224 and/or the linear motion mechanism 280 when performing a pivot operation will be described in detail.

Herein, in a pivot operation in the microscope apparatus 10 according to the first embodiment, the distance between the microscope section 110 and the tilt reference point (that is, the pivot point) set in the approximate center of the interior of the subject's eye 503 is fixed. However, in the microscope apparatus 20 according to the second embodiment, it is possible to perform a pivot operation with a variable distance between the microscope section 210 and the pivot point. In the microscope apparatus 20, by combining an operation of moving the microscope section 210 in the direction of the optical axis in a state in which the optical axis of the microscope section 210 always passes through the pivot point (hereinafter also called an optical axis direction movement operation) and an operation of tilting the microscope section 210 in a state in which the optical axis of the microscope section 210 always passes through the pivot point while the distance between the microscope section 210 and the pivot point remains fixed (in other words, a tilting operation in the microscope apparatus 10 according to the first embodiment; hereinafter also called a fixed-distance tilting operation), it becomes possible to perform a pivot operation with a variable distance between the microscope section 210 and the pivot point as above.

First, the optical axis direction movement operation will be described. At this point, assume that the microscope section 210 is being rotated by the elevation apparatus 270 in accordance with instruction input by the surgeon, such that its optical axis is inclined by an angle α in the X direction and by an angle in the Y direction with respect to a pivot point O. FIGS. 11 to 14 are diagrams for explaining a state in which the microscope section 210 rotates such that the optical axis is inclined by an angle α in the X direction and by an angle β in the Y direction with respect to the pivot point O.

Figure 11:
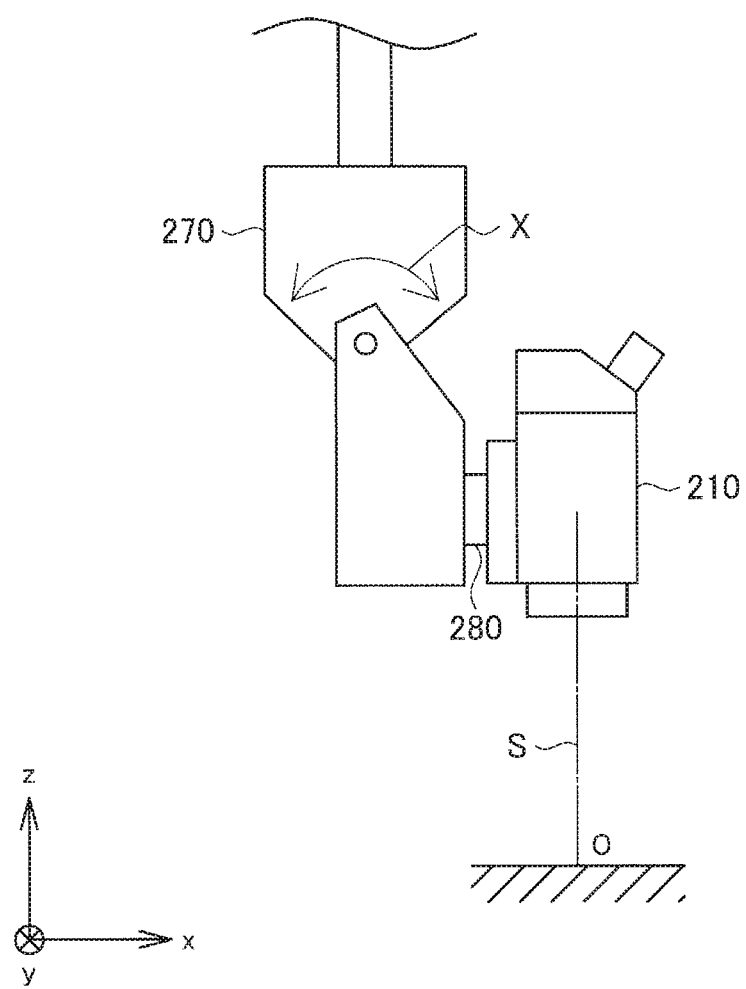
FIG. 11 is a diagram for explaining a state in which the microscope section rotates such that the optical axis is inclined by an angle $\alpha$ in the X direction and by an angle $\beta$ in the Y direction with respect to a pivot point O.
Figure 12:
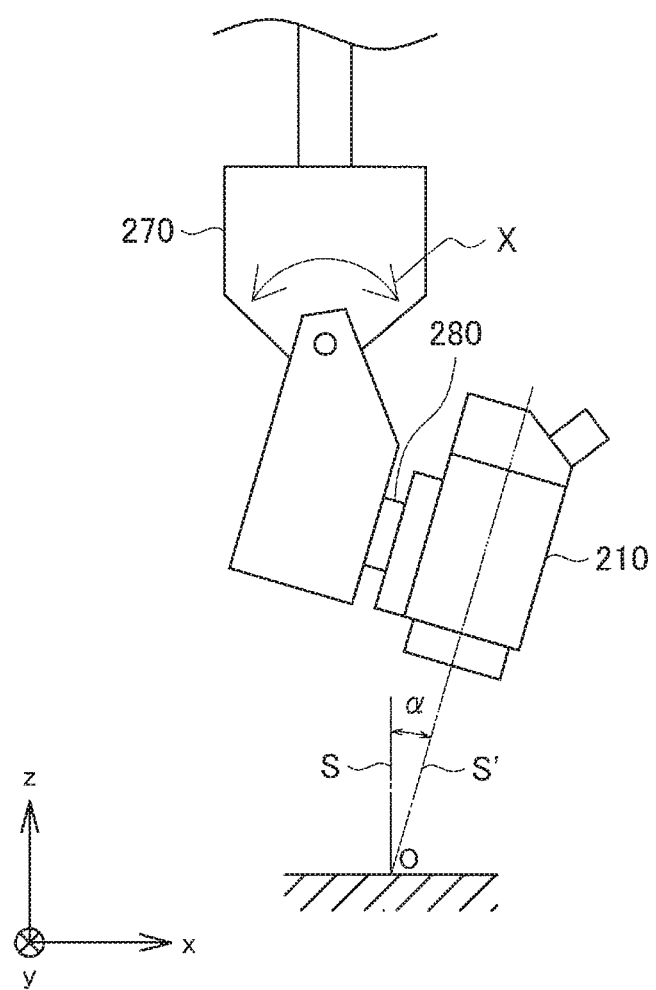
FIG. 12 is a diagram for explaining a state in which the microscope section rotates such that the optical axis is inclined by an angle $\alpha$ in the X direction and by an angle $\beta$ in the Y direction with respect to a pivot point O.

FIGS. 11 and 12 illustrate a view of the microscope section 210 as seen from the y-axis direction. As illustrated in FIG. 11, the state in which the optical axis of the microscope section 210 is substantially parallel to the vertical direction is taken to be an angle of 0. At this time, the state in which the optical axis of the microscope section 210 is inclined by an angle α in the x-z plane from the state of being substantially parallel to the vertical direction as illustrated in FIG. 12 corresponds to a state in which the microscope section 210 has rotated such that the optical axis is inclined by the angle α in the X direction with respect to the pivot point O.

Figure 13:
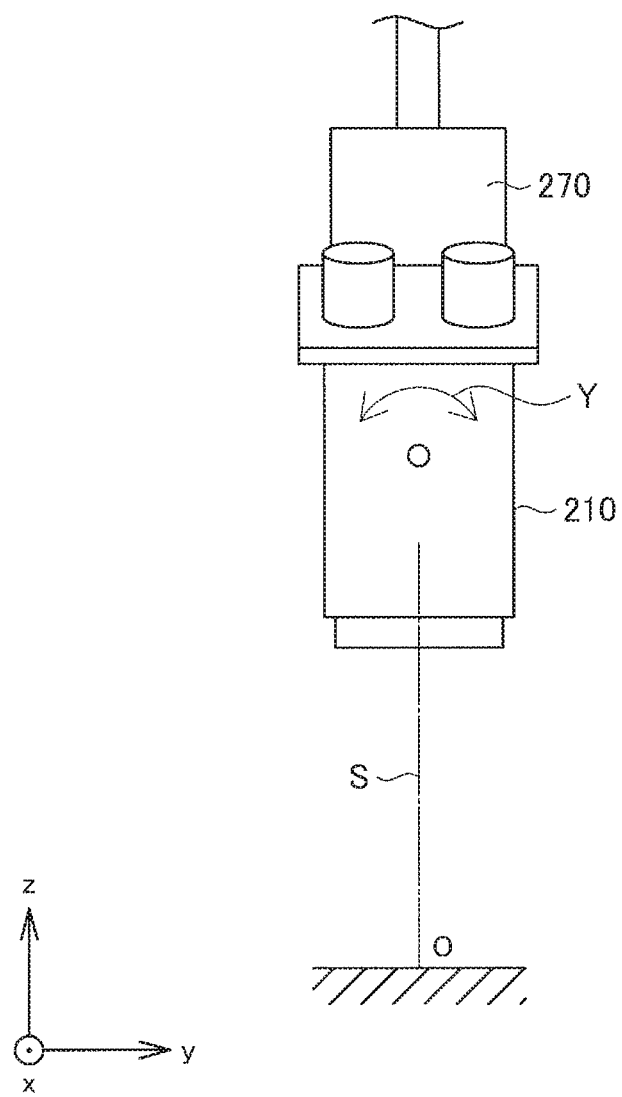
FIG. 13 is a diagram for explaining a state in which the microscope section rotates such that the optical axis is inclined by an angle $\alpha$ in the X direction and by an angle $\beta$ in the Y direction with respect to a pivot point O.
Figure 14:
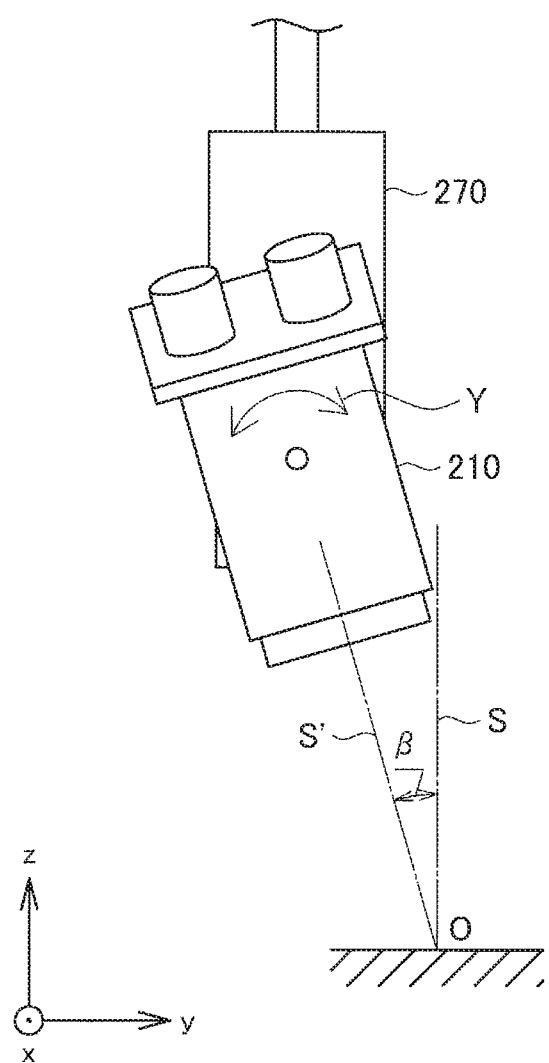
FIG. 14 is a diagram for explaining a state in which the microscope section rotates such that the optical axis is inclined by an angle $\alpha$ in the X direction and by an angle $\beta$ in the Y direction with respect to a pivot point O.

Moreover, FIGS. 13 and 14 illustrate a view of the microscope section 210 as seen from the x-axis direction. As illustrated in FIG. 13, the state in which the optical axis of the microscope section 210 is substantially parallel to the vertical direction is taken to be an angle of 0. At this time, the state in which the optical axis of the microscope section 210 is inclined by an angle β in the y-z plane from the state of being substantially parallel to the vertical direction as illustrated in FIG. 14 corresponds to a state in which the microscope section 210 has rotated such that the optical axis is inclined by the angle β in the Y direction with respect to the pivot point O.

In FIGS. 11 and 13, the optical axis of the microscope section 210 in the state in which the optical axis of the microscope section 210 is substantially parallel to the vertical direction is designated the optical axis S, while the optical axis of the microscope section 210 in the state in which the microscope section 210 has rotated such that the optical axis is inclined by the angle α in the X direction and the angle β in the Y direction with respect to the pivot point O is designated the optical axis S'.

Assume that, in the state in which the microscope section 210 has rotated such that its optical axis is inclined by the angles α and β, the microscope section 210 is moved a distance P1 in the vertical direction by the linear motion mechanism 224 and/or the linear motion mechanism 280 in accordance with instruction input by the surgeon. At this time, by appropriately driving the x-y apparatus 260, it is possible to perform an operation of moving the microscope section 210 in the direction of its optical axis by a distance corresponding to the distance P1 in a state in which the optical axis of the microscope section 210 passes through the pivot point O (that is, an optical axis direction movement operation by a distance corresponding to the distance P1).

To achieve such an operation, specifically, when the microscope section 210 has moved the distance P1 in the vertical direction, it is sufficient for the x-y apparatus 260 to move the microscope section 210 in the horizontal plane such that the microscope section 210 is positioned on the optical axis S'. The movement amount in the horizontal plane of the microscope section 210 by the x-y apparatus 260 can be obtained by geometric operations like the following.

Figure 15:
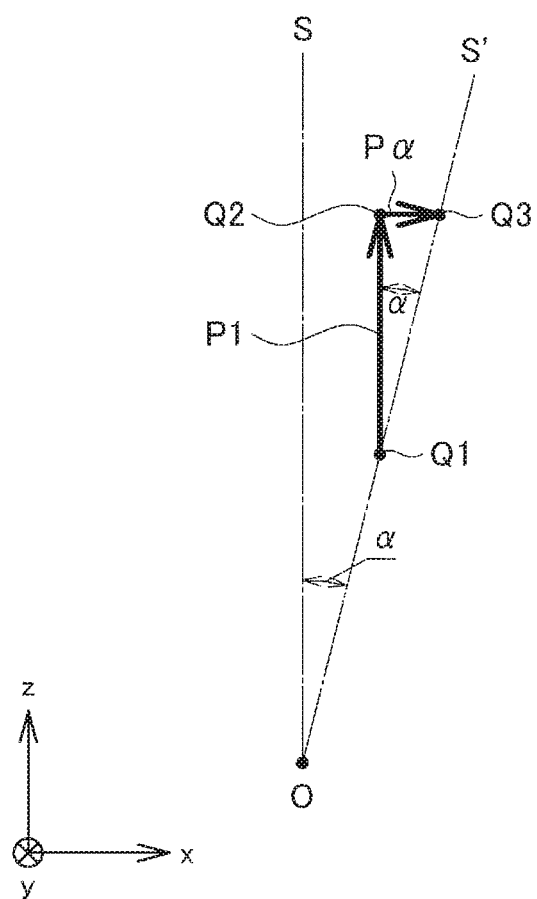
FIG. 15 is a diagram for explaining a movement amount in the x-axis direction of the microscope section by an x-y apparatus.

First, the movement of the microscope section 210 in the x-axis direction will be considered. FIG. 15 is a diagram for explaining the movement amount in the x-axis direction of the microscope section 210 by the x-y apparatus 260. FIG. 15 illustrates the geometric relationships of the optical axis S, the optical axis S', and the movement distance P1 in the vertical direction in the x-z plane. As illustrated in FIG. 15, let Q1 be the point indicating the initial position of the microscope section 210, and let Q2 be the point after the microscope section 210 moves by P1 in the vertical direction from the point Q1. When the microscope section 210 moves by the distance P1 in the vertical direction, to make the microscope section 210 be positioned on the optical axis S', it is sufficient for the x-y apparatus 260 to move the microscope section 210 in the x-axis direction by a distance Pα between the point Q2 and the optical axis S' in the x-axis direction and cause the microscope section 210 to be positioned at a point Q3 on the optical axis S' at the same height as the point Q2. Herein, as illustrated in FIG. 15, the relationship Pα=P1×tan α holds from geometric considerations. Since α and P1 are quantities corresponding to the instruction input of the surgeon and are known values, Pα can be obtained from the above relationship.

Figure 16:
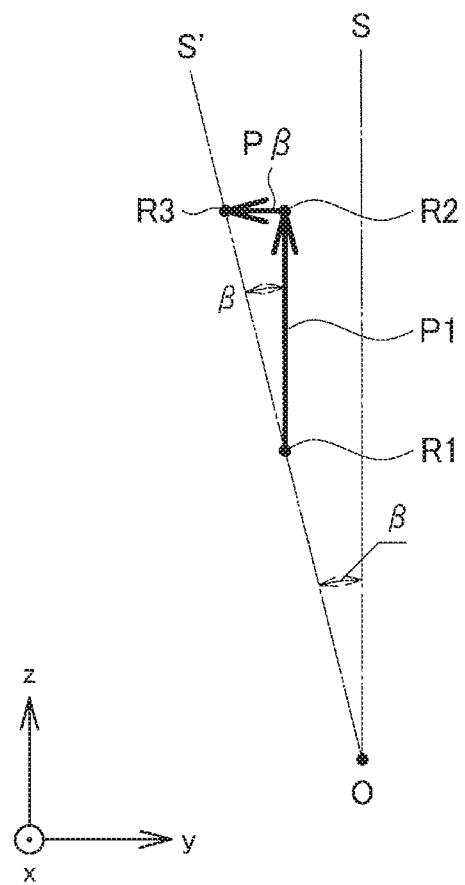
FIG. 16 is a diagram for explaining a movement amount in the y-axis direction of the microscope section by the x-y apparatus.

Next, the movement of the microscope section 210 in the y-axis direction will be considered. FIG. 16 is a diagram for explaining the movement amount in the y-axis direction of the microscope section 210 by the x-y apparatus 260. FIG. 16 illustrates the geometric relationships of the optical axis S, the optical axis S', and the movement distance P1 in the vertical direction in the y-z plane. As illustrated in FIG. 16, let R1 be the point indicating the initial position of the microscope section 210, and let R2 be the point after the microscope section 210 moves by P1 in the vertical direction from the point R1. When the microscope section 210 moves by the distance P1 in the vertical direction, to make the microscope section 210 be positioned on the optical axis S', it is sufficient for the x-y apparatus 260 to move the microscope section 210 in the y-axis direction by a distance Pβ between the point R2 and the optical axis S' in the y-axis direction and cause the microscope section 210 to be positioned at a point R3 on the optical axis S' at the same height as the point R2. Herein, as illustrated in FIG. 16, the relationship Pβ=P1×tan β holds from geometric considerations. Since β and P1 are quantities corresponding to the instruction input of the surgeon and are known values, Pβ can be obtained from the above relationship.

In the case in which the microscope section 210 is moved by the distance P1 in the vertical direction by the linear motion mechanism 224 and/or the linear motion mechanism 280 in the state in which the microscope section 210 has rotated such that the optical axis is inclined by the angles α and β, the control circuit of the x-y apparatus 260 computes Pα and Pβ using the method described above. Subsequently, the control circuit drives the motor such that the microscope section 210 moves by Pα in the x-axis direction and Pβ in the y-axis direction. With this arrangement, the optical axis direction movement operation may be achieved.

Next, the fixed-distance tilting operation will be described. At this point, assume that as a result of adjusting the position and attitude of the microscope section 210 in accordance with instruction input by the surgeon, the optical axis of the microscope section 210 is in a state of being substantially parallel to the vertical direction, and the optical axis is in a state of passing through the pivot point O. In addition, at this time, assume that the distance between the microscope section 210 and the pivot point O has also been adjusted to a predetermined distance. In this state, assume that the microscope section 210 is rotated by the elevation apparatus 270 in accordance with instruction input by the surgeon such that the optical axis is inclined by a predetermined angle. At this time, by appropriately driving the x-y apparatus 260, the linear motion mechanism 224, and/or the linear motion mechanism 280, it is possible to make the microscope section 210 perform a fixed-distance tilting operation.

To achieve such an operation, specifically, in the case in which the microscope section 210 has been rotated such that the optical axis is inclined by a predetermined angle, it is sufficient for each of the x-y apparatus 260, the linear motion mechanism 224 and/or the linear motion mechanism 280 to move the microscope section 210 in the horizontal direction and the vertical direction such that the optical axis of the microscope section 210 passes through the pivot point. The movement amounts in the horizontal direction and the vertical direction of the microscope section 210 by the x-y apparatus 260, the linear motion mechanism 224 and/or the linear motion mechanism 280 can be obtained by geometric operations like the following.

Figure 17:
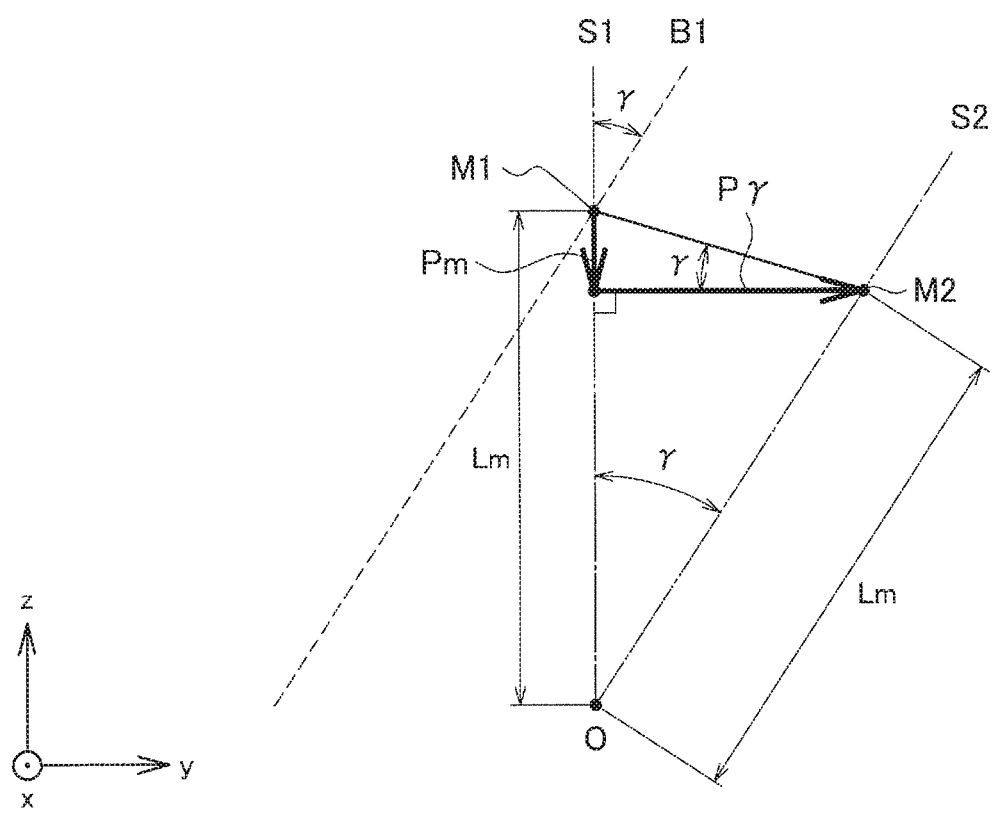
FIG. 17 is a diagram for explaining movement amounts in the horizontal direction and the vertical direction of the microscope section by the x-y apparatus, a linear motion mechanism and/or a linear motion mechanism.

FIG. 17 is a diagram for explaining movement amounts in the horizontal direction and the vertical direction of the microscope section 210 by the x-y apparatus 260, the linear motion mechanism 224 and/or the linear motion mechanism 280. Herein, for the sake of simplicity, a case of rotating the microscope section 210 by the elevation apparatus 270 such that the optical axis is tilted by an angle γ only in the Y direction will be considered. Assuming that the optical axis S1 is the optical axis of the microscope section 210 substantially parallel to the vertical direction before tilting, that an optical axis B1 is the optical axis of the microscope section 210 after rotating the microscope section 210 and tilting by the angel γ by the elevation apparatus 270, and that an optical axis S2 is the optical axis of the microscope section 210 after tilting the optical axis by the angle γ and moving in the horizontal direction and the vertical direction until the optical axis passes through the pivot point O (that is, at the position that is ultimately desired for positioning), the geometric relationships of the optical axis S1, the optical axis B1, the optical axis S2, and the angle γ in the y-z plane are as illustrated in FIG. 17. FIG. 17 illustrates the geometric relationships of the optical axis S1, the optical axis B1, the optical axis S2, and the angle γ in the y-z plane.

As illustrated in FIG. 17, let M1 be the point indicating the initial position of the microscope section 210 on the optical axis S1, and let M2 be the point indicating the position where it is ultimately desirable to position the microscope section 210 on the optical axis S2. At this time, the distance from the pivot point O to the point M1 and the distance from the pivot point O to the point M2 are the same (let this distance be Lm). Also, the optical axis B1 can be described as a straight line passing through the point M1 and parallel to the optical axis S2.

When the microscope section 210 is rotated by the elevation apparatus 270 such that the optical axis is tilted by the angle γ from the state of being substantially parallel to the vertical direction, to reach a state in which the optical axis of the microscope section 210 passes through the pivot point O while also keeping the distance between the microscope section 210 and the pivot point O fixed, it is sufficient to move the microscope section 210 from the point M1 to the point M2 by the x-y apparatus 260, the linear motion mechanism 224 and/or the linear motion mechanism 280. Referring to FIG. 17, the distance Pγ in the y-axis direction between the point M1 and the point M2 is Pγ=Lm×sin γ, and the distance Pm in the z-axis direction between the point M1 and the point M2 is Pm=Lm−Lm×cos γ. Since γ and Lm are quantities corresponding to the instruction input of the surgeon and are known values, Pγ and Pm can be obtained from the above relationship.

Figure 18:
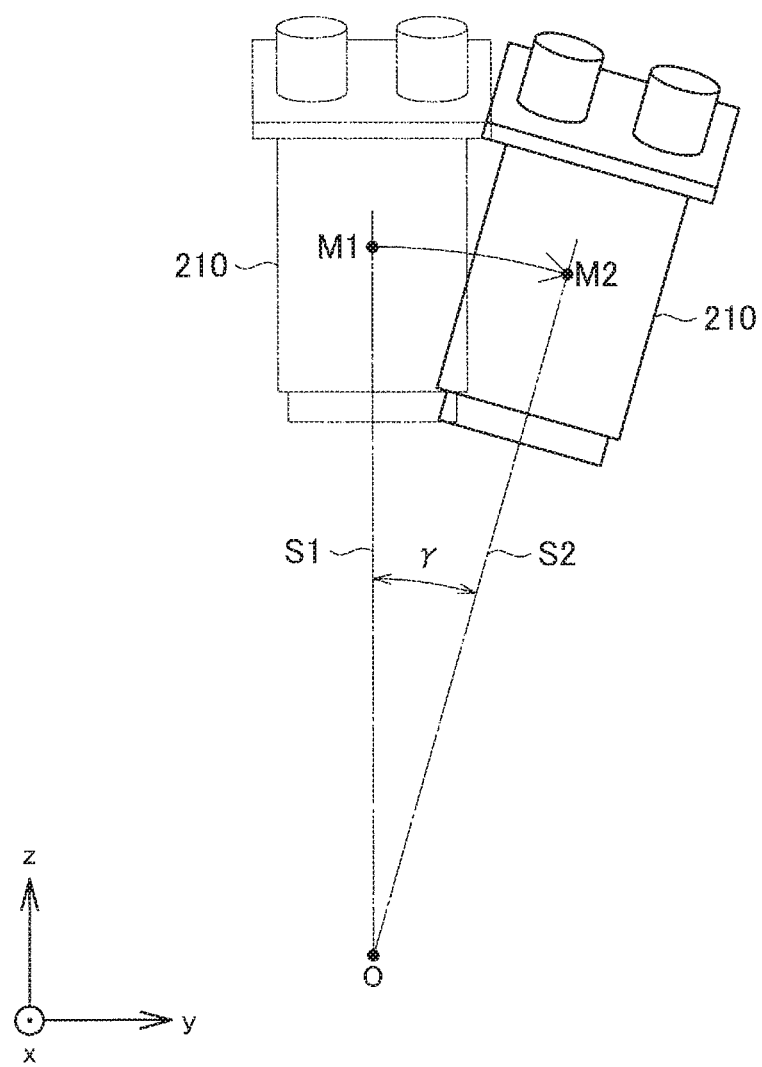
FIG. 18 is a diagram illustrating the motion of the microscope section during a fixed-distance tilting operation in a microscope apparatus according to a second embodiment.

In the case in which the microscope section 210 is rotated by the elevation apparatus 270 such that the optical axis is tilted by the angle γ from a state of being substantially parallel to the vertical direction, the control circuits of the x-v apparatus 260, the linear motion mechanism 224 and/or the linear motion mechanism 280 use the method described above to compute each of Pm and Pγ. Subsequently, these control circuits drive each of the motors such that the microscope section 210 moves by Pm in the z-axis direction and by Pγ in the y-axis direction. With this arrangement, the fixed-distance tilting operation may be achieved. FIG. 18 is a diagram illustrating the motion of the microscope section 210 during the fixed-distance tilting operation in the microscope apparatus 20 according to the second embodiment.

Note that herein, a case of rotating the microscope section 210 by the elevation apparatus 270 such that the optical axis is tilted by the angle γ only in the Y direction is described for the sake of simplicity, but even in the case of rotating the microscope section 210 such that the optical axis is tilted in the X direction, the movement amounts in the horizontal direction and the vertical direction of the microscope section 210 by the x-y apparatus 260, the linear motion mechanism 224 and/or the linear motion mechanism 280 can be computed similarly. In the case in which the tilting direction of the optical axis of the microscope section 210 by the elevation apparatus 270 is an arbitrary direction, it is sufficient to decompose the tilting angle into an X direction and a Y direction, and compute the movement amounts in the horizontal direction and the vertical direction of the microscope section 210 by the x-y apparatus 260, the linear motion mechanism 224 and/or the linear motion mechanism 280 for each.

By having the control circuits of the x-y apparatus 260, the elevation apparatus 270, the linear motion mechanism 224 and/or the linear motion mechanism 280 cooperate and execute the two operations described above (the optical axis direction movement operation and the fixed-distance tilting operation) at the same time, in the microscope apparatus 20, a pivot operation with a variable distance between the microscope section 210 and the pivot point may be achieved.

In the second embodiment, such a microscope apparatus 20 is used to perform eye surgery in a state with the pivot point set to the approximate center of the interior of the subject's eye. With this arrangement, similarly to the first embodiment, it becomes possible to smoothly perform an operation of tilting the microscope section 210 such that a favorable red reflex is obtained in correspondence with the movement of the subject's eye. Furthermore, according to the second embodiment, at this time, since the distance between the microscope section 210 and the pivot point is variable, the degree of freedom in the position of the microscope section 210 when tilting the microscope section 210 is improved, making it possible to further improve convenience for the surgeon, such as moving the microscope section 210 to a position that interferes less with treatments by the surgeon, for example.

Note that in the microscope apparatus 20, whether or not to perform a pivot operation preferably is switched appropriately by instruction input by the surgeon through an input apparatus such as a switch, for example. For example, at the setting stage before starting surgery, the pivot operation is turned off. With this arrangement, the surgeon is able to move the microscope section 210 freely, making it possible to dispose the microscope section 210 at a suitable position with respect to the subject's eye. Subsequently, setting ends, surgery is started, and it is sufficient to turn on the pivot operation while in the middle of observing the subject's eye with the microscope section 210. With this arrangement, during surgery, smooth movement of the microscope section 210 that tracks the movement of the subject's eye may be achieved.

(2-3. Modification)

One modification of the second embodiment will be described. In the exemplary configuration described above, the microscope apparatus 20 is provided with the x-y apparatus 260 and the linear motion mechanism 224, and by causing these to operate appropriately, a pivot operation is achieved. However, the second embodiment is not limited to such an example, and the microscope apparatus 20 may be configured in any way insofar as the pivot operation is achievable. For example, by innovating in the configuration of the holding section 220, the microscope apparatus 20 may be configured to be capable of the pivot operation without being provided with the x-v apparatus 260 and the linear motion mechanism 224. Herein, as one modification of the second embodiment, a microscope apparatus having such an other configuration will be described.

Figure 19:
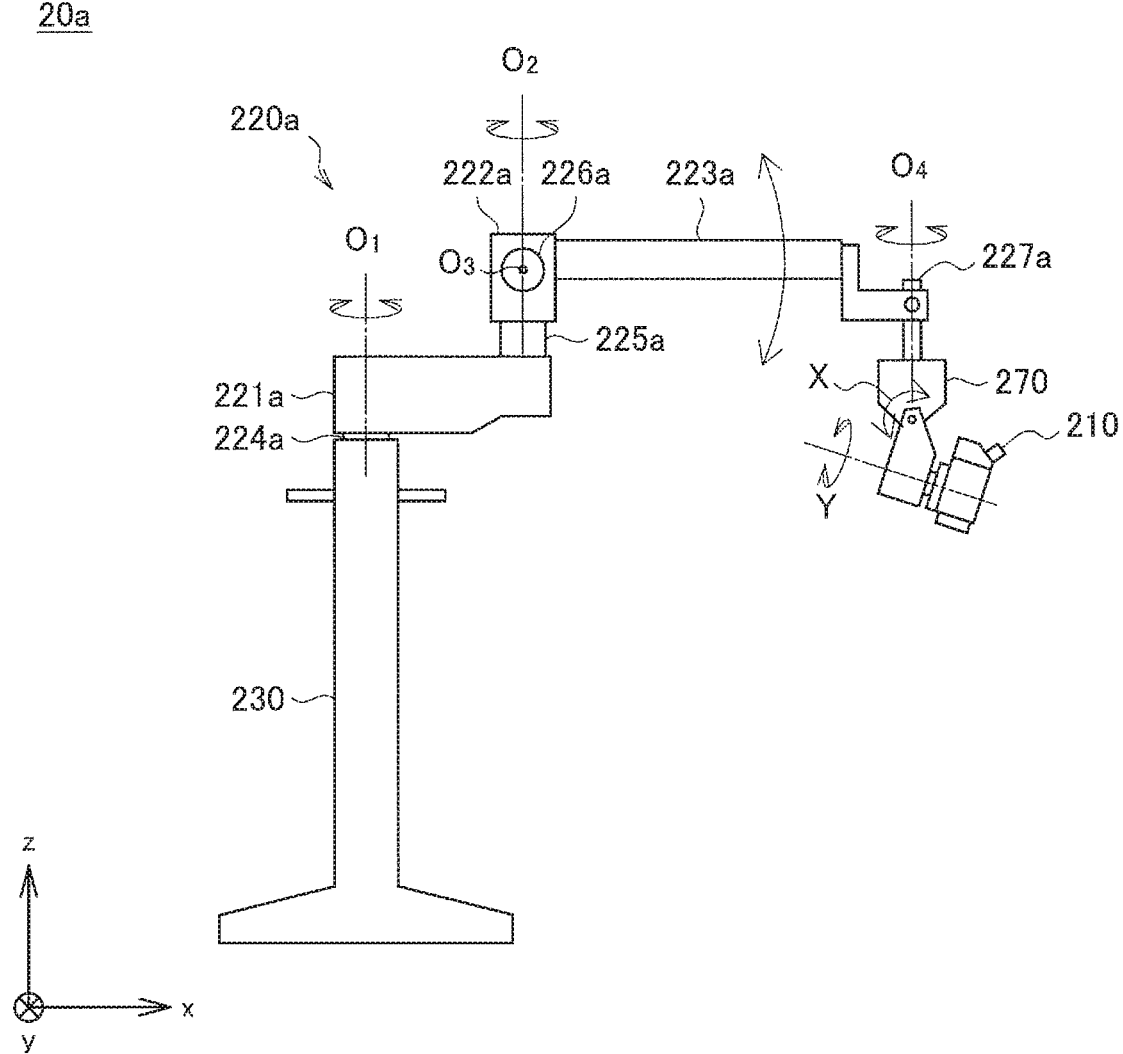
FIG. 19 is a diagram schematically illustrating an overall configuration of a microscope apparatus having an other configuration in one modification of the second embodiment.

FIG. 19 is a diagram schematically illustrating an overall configuration of a microscope apparatus having an other configuration in one modification of the second embodiment. Referring to FIG. 19, the microscope apparatus 20a according to the present modification is provided with the microscope section 210 for performing magnified observation of a subject's eye, an arm section 220a (holding section 220a) that holds the microscope section 210, the elevation apparatus 270, provided between the holding section 220a and the microscope section 210, capable of rotating the microscope section 210 about a rotation axis parallel to the y-axis (that is, in the X direction of the diagram) and about a rotation axis parallel to the y-axis (that is, in the Y direction of the diagram), the linear motion mechanism 280, provided between the elevation apparatus 270 and the microscope section 210, capable of moving the microscope section 210 in the z-axis direction, the base section 230 to which the base end of the holding section 220a is connected that supports the microscope section 210 and the holding section 220a, and the footswitch 240 for inputting various instructions into the microscope apparatus 20a. Since the configurations and functions of the microscope section 210, the base section 230, the footswitch 240, the elevation apparatus 270, and the linear motion mechanism 280 are similar to the those of the microscope apparatus 20 described above, a detailed description is omitted here.

The holding section 220a includes multiple movable sections (a first rotation axis section 224a, a second rotation axis section 225a, a third rotation axis section 226a, and a fourth rotation axis section 227a) and multiple links (a first arm 221a, a second arm 222a, and a third arm 223a) joined to each other through these multiple movable sections.

The base section 230 rotatably supports the first arm 221a through the first rotation axis section 224a treating the z-axis direction as the rotation axis direction. Hereinafter, the rotation axis of the first rotation axis section 224a will also be designed the first axis $O_1$.

The first arm 221a extends in the horizontal direction. On the front end of the first arm 221a, the base end of the second arm 222a is connected through the second rotation axis section 225a that treats the z-axis direction as the rotation axis direction. In other words, the first arm 221a rotatably supports the second arm 222a through the second rotation axis section 225a treating the z-axis direction as the rotation axis direction. Hereinafter, the rotation axis of the second rotation axis section 225a will also be designed the second axis $O_2$.

The second arm 222a extends in the vertical direction. On the front end of the second arm 222a, the base end of the third arm 223a is connected through the third rotation axis section 226a that treats the y-axis direction as the rotation axis direction. In other words, the second arm 222a rotatably supports the third arm 223a through the third rotation axis section 226a treating the y-axis direction as the rotation axis direction. Hereinafter, the rotation axis of the third rotation axis section 226a will also be designed the third axis $O_3$.

The third arm 223a extends in the horizontal direction. On the front end of the third arm 223a, the elevation apparatus 270 and the microscope section 210 are connected through the fourth rotation axis section 227a that treats the z-axis direction as the rotation axis direction.

By having the configuration described above, in the holding section 220a, by causing the configuration farther on the from end side than the third rotation axis section 226a to rotate about the third rotation axis section 226a, the position in the vertical direction of the microscope section 210 can be adjusted. Also, by causing the configuration farther on the front end side than the first rotation axis section 224a to rotate about the first rotation axis section 224a while also causing the configuration farther on the front end side than the second rotation axis section 225a to rotate about the second rotation axis section 225a, the position in the horizontal plane of the microscope section 210 can be adjusted. In this way, in the microscope apparatus 20a, by appropriately changing the attitude of the holding section 220a by the first rotation axis section 224a, the second rotation axis section 225a, and the third rotation axis section 226a, the three-dimensional position of the microscope section 210 can be adjusted. Also, by causing the configuration farther on the front end side than the fourth rotation axis section 227a to rotate about the fourth rotation axis section 227a, the direction of the microscope section 210 treating the z-axis direction as the rotation axis (that is, the direction of the field of view by the microscope section 210) can be adjusted.

Note that the operations of the rotation axis sections in the holding section 220a may be performed manually or electrically by providing actuators (such as a motor and a control circuit that drives the motor, for example) in these configurations. In the case in which the operations of the rotation axis sections are performed electrically, the operations preferably are executed in accordance with instruction input by the surgeon through the footswitch 240.

As described above, since the third rotation axis section 226a is able to adjust the position in the vertical direction of the microscope section 210, from the perspective of the movement of the microscope section 210, the third rotation axis section 226a may be said to have a function similar to the linear motion mechanism 224 in the microscope apparatus 20. Also, since the first rotation axis section 224a and the second rotation axis section 225a are able to adjust the position in the horizontal plane of the microscope section 210, from the perspective of the movement of the microscope section 210, the first rotation axis section 224a and the second rotation axis section 225a may be said to have a function similar to the x-y apparatus 260 in the microscope apparatus 20. In the present modification, by appropriately controlling the operations of the first rotation axis section 224a, the second rotation axis section 225a, and the third rotation axis section 226a, it is possible to perform a pivot operation. In other words, in the present modification, a tilting section may be realized by the first rotation axis section 224a, the second rotation axis section 225a, and the third rotation axis section 226a.

Hereinafter, the operations of the first rotation axis section 224a, the second rotation axis section 225a, and the third rotation axis section 226a when performing a pivot operation will be described in detail. Note that likewise in the microscope apparatus 20a, similarly to the microscope apparatus 20, by combining the optical axis direction movement operation and the fixed-distance tilting operation, it is possible to perform a pivot operation with a variable distance between the microscope section 210 and the pivot point.

At this point, for the sake of simplicity, only the operations of the first rotation axis section 224a, the second rotation axis section 225a, and the third rotation axis section 226a when performing the optical axis direction movement operation will be described. A description of the operations of the first rotation axis section 224a, the second rotation axis section 225a, and the third rotation axis section 226a when performing the fixed-distance tilting operation will be omitted, but it is possible to perform the fixed-distance tilting operation similarly to the case of the microscope apparatus 20.

At this point, assume that the microscope section 210 is being rotated by the elevation apparatus 270 in accordance with instruction input by the surgeon, such that its optical axis is inclined by an angle α in the X direction and by an angle β in the Y direction with respect to a pivot point O. In this state, in the case of rotating the configuration farther on the front end side than the third rotation axis section 226a about the third rotation axis section 226a by an angle θ' downward in accordance with instruction input by the surgeon, by causing the first rotation axis section 224a and the second rotation axis section 225a to operate and appropriately move the microscope section 210 in the horizontal plane, the microscope section 210 can be positioned on the same optical axis as the original state (that is, the optical axis direction movement operation can be performed).

Figure 20:
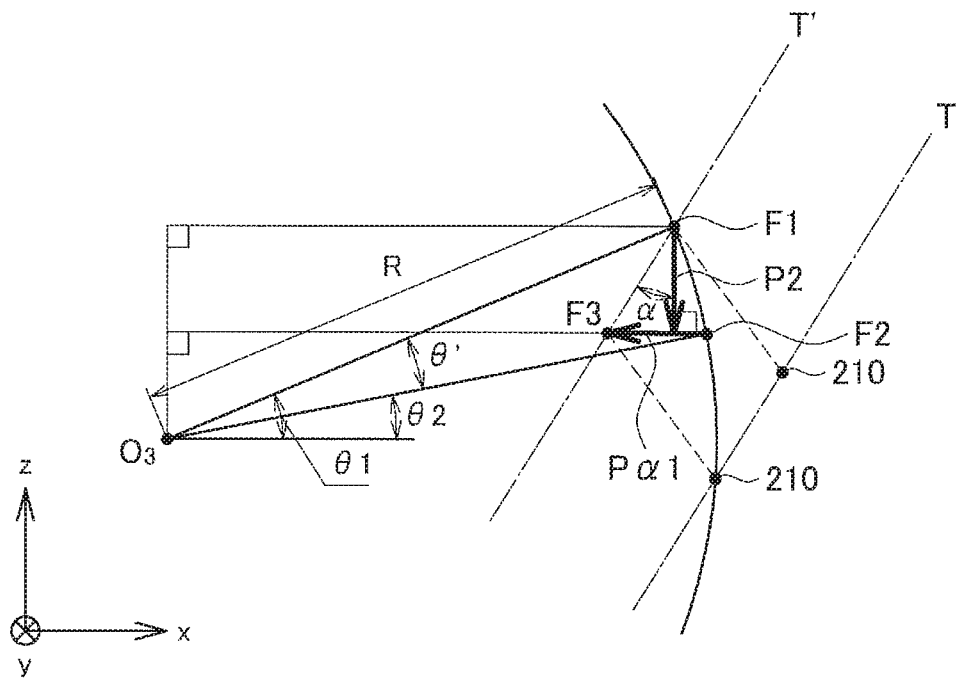
FIG. 20 is a diagram for explaining a movement amount in the x-axis direction of the microscope section by a first rotation axis section and a second rotation axis section.

First, the movement of the microscope section 210 in the x-axis direction will be considered. FIG. 20 is a diagram for explaining the movement amount in the x-axis direction of the microscope section 210 by the first rotation axis section 224a and the second rotation axis section 225a.

In FIG. 20, the optical axis T represents the optical axis of the microscope section 210 (simply illustrated as a point in FIG. 20) before performing an operation of rotating about the third rotation axis section 226a, and the optical axis T' represents the optical axis of the microscope section 210 after performing the operation of rotating about the third rotation axis section 226a. Also, the point F1 is a point representing the position of the front end of the third arm 223a before performing the operation of rotating about the third rotation axis section 226a, and the point F2 is a point representing the position of the front end of the third arm 223a after performing the operation of rotating about the third rotation axis section 226a in the case of not performing the optical axis direction movement operation.

As illustrated in FIG. 20, the point F3 is taken to be the position of the front end of the third arm 223a in the case in which the microscope section 210 is positioned on the optical axis T after performing the operation of rotating about the third rotation axis section 226a. In other words, to make the microscope section 210 be positioned on the optical axis T (that is, to perform the optical axis direction movement operation) after performing the operation of rotating about the third rotation axis section 226a, when performing the operation of rotating about the third rotation axis section 226a, it is sufficient to move the point F2 to the point F3 with the first rotation axis section 224a and the second rotation axis section 225a.

The movement from the point F2 to the point F3 is a translation in the x-axis direction, and let Pα1 be its movement amount. If R is the length from the third rotation axis section 226a to the third arm 223a, θ1 is the angle from the horizontal direction before performing the operation of rotating about the third rotation axis section 226a in the third arm 223a, θ2 is the angle from the horizontal direction after performing the operation of rotating about the third rotation axis section 226a in the third arm 223a, and P2 is the length of the normal dropped from the point F1 to a straight line joining the points F2 and F3, then the relationships Pα1=R(cos θ1−cos θ2)+P2×tan α and P2=R(sin θ1−sin θ2) hold from geometric considerations. Also, θ'=θ1−θ2. Since the length R is a fixed value prescribed by the structure of the holding section 220a, α is a quantity according to the instruction input of the surgeon, and both are known values, Pα1 can be obtained from the above relationships.

Figure 21:
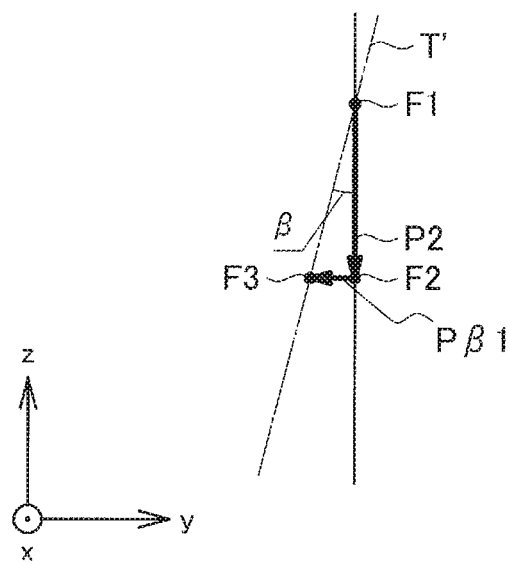
FIG. 21 is a diagram for explaining a movement amount in the y-axis direction of the microscope section by a first rotation axis section and a second rotation axis section.

Next, the movement of the microscope section 210 in the y-axis direction will be considered. FIG. 21 is a diagram for explaining the movement amount in the y-axis direction of the microscope section 210 by the first rotation axis section 224a and the second rotation axis section 225a.

In FIG. 21, the meanings of the optical axis T', the point F1, the point F2, the point F3, and the length P2 are similar to FIG. 20. In order for the microscope section 210 to be positioned on the optical axis T after performing the operation of rotating about the third rotation axis section 226a (that is, to perform the optical axis direction movement operation), after performing the operation of rotating about the third rotation axis section 226a, it is sufficient to move the point F2 to the point F3 with the first rotation axis section 224a and the second rotation axis section 225a.

The movement from the point F2 to the point F3 is a translation in the y-axis direction, and let Pβ1 be its movement amount. Referring to FIG. 21, the relationship Pβ1=P2×tan β holds from geometric considerations. For P2, as described above, P2=R(sin θ1−sin θ2), which can be calculated. Also, since the angle β is a quantity corresponding to the instruction input of the surgeon and is a known value, Pβ1 can be obtained from the above relationship.

In the case in which the microscope section 210 moves downward by an operation of rotating about the third rotation axis section 226a in the state in which the microscope section 210 has rotated such that the optical axis is inclined by the angles α and β, the control circuits of the first rotation axis section 224a and the second rotation axis section 225a compute Pα1 and Pβ1 using the method described above. Subsequently, these control circuits drive each of the motors such that the microscope section 210 moves by Pα1 in the x-axis direction and Pβ1 in the y-axis direction. With this arrangement, the optical axis direction movement operation may be achieved.

As described above, for the sake of simplicity, a description of the operations of the first rotation axis section 224a and the second rotation axis section 225a when performing the fixed-distance tilting operation is omitted, but since the third rotation axis section 226a in the microscope apparatus 20a has functions similar to the linear motion mechanism 224 in the microscope apparatus 20 and since the first rotation axis section 224a and the second rotation axis section 225a in the microscope apparatus 20a have functions similar to the x-y apparatus 260 in the microscope apparatus 20, their cooperation makes it possible to perform the fixed-distance tilting operation in the microscope apparatus 20a similarly to the case of the microscope apparatus 20.

In this way, by having the control circuits of the elevation apparatus 270, the first rotation axis section 224a, the second rotation axis section 225a, and the third rotation axis section 226a cooperate and execute these two operations (the optical axis direction movement operation and the fixed-distance tilting operation) at the same time, a pivot operation with a variable distance between the microscope section 210 and the pivot point may also be achieved in the microscope apparatus 20a. Consequently, even in eye surgery using the microscope apparatus 20a, advantageous effects similar to the microscope apparatus 20 can be obtained. Namely, it becomes possible to smoothly perform the operation of tilting the microscope section 210 while also further improving convenience for the surgeon.

Note that more detailed configurations and functions of the microscope apparatus 20 and 20a described above can be found by referencing the description in JP H5-253246A.

Herein, in the second embodiment, it is possible for the microscope apparatus to have yet another configuration. As described above, in the microscope apparatus 20, the optical axis direction movement operation and the fixed-distance tilting operation are achieved by the elevation apparatus 270, the linear motion mechanism 224 and/or the linear motion mechanism 280 that move the microscope section 210 in the vertical direction, and the x-y apparatus 260 that moves the microscope section 210 in the horizontal plane. Also, in the microscope apparatus 20a, the optical axis direction movement operation and the fixed-distance tilting operation are achieved by the elevation apparatus 270, the third rotation axis section 226a that moves the microscope section 210 in the vertical direction, and the first rotation axis section 224a and second rotation axis section 225a that move the microscope section 210 in the horizontal plane. In this way, in the second embodiment, if the microscope apparatus is provided with the elevation apparatus 270, a vertical direction movement mechanism that moves the microscope section 210 in the vertical direction, and a horizontal plane movement mechanism that moves the microscope section 210 in the horizontal plane, a tilting section may be configured by the elevation apparatus 270, the vertical direction movement mechanism, and the horizontal plane movement mechanism, and with such a tilting section, the optical axis direction movement operation and the fixed-distance tilting operation (that is, a pivot operation with a variable distance between the microscope section 210 and the pivot point) may be achieved. In other words, in the second embodiment, it is sufficient for the microscope apparatus to be configured to include the elevation apparatus 270, the vertical direction movement mechanism, and the horizontal plane movement mechanism.

3. Third Embodiment

A third embodiment of the present disclosure will be described. In the third embodiment, a microscope apparatus including yet another configuration capable of a pivot operation is provided.

Herein, the microscope apparatus 10, 20, and 20a according to the first embodiment and the second embodiment described above include the optical microscope sections 110 and 210. In contrast, the microscope apparatus according to the third embodiment described below includes an electronic imaging microscope section that includes an image sensor and takes an image with the image sensor. In a microscope apparatus including an electronic imaging microscope section, an image of the surgical site (in other words, the subject's eye in the case of eye surgery) taken by the microscope section appears on a display apparatus installed inside the operating room, and the surgeon observes a magnified view of the surgical site through the image on the display apparatus. In this way, in a microscope apparatus including an electronic imaging microscope section, an observation system for surgery may be configured by the microscope apparatus and the display apparatus. In the third embodiment, the configuration of this observation system will be described while simultaneously describing the configuration of the microscope apparatus.

(3-1. Configuration of Observation System)

Figure 22:
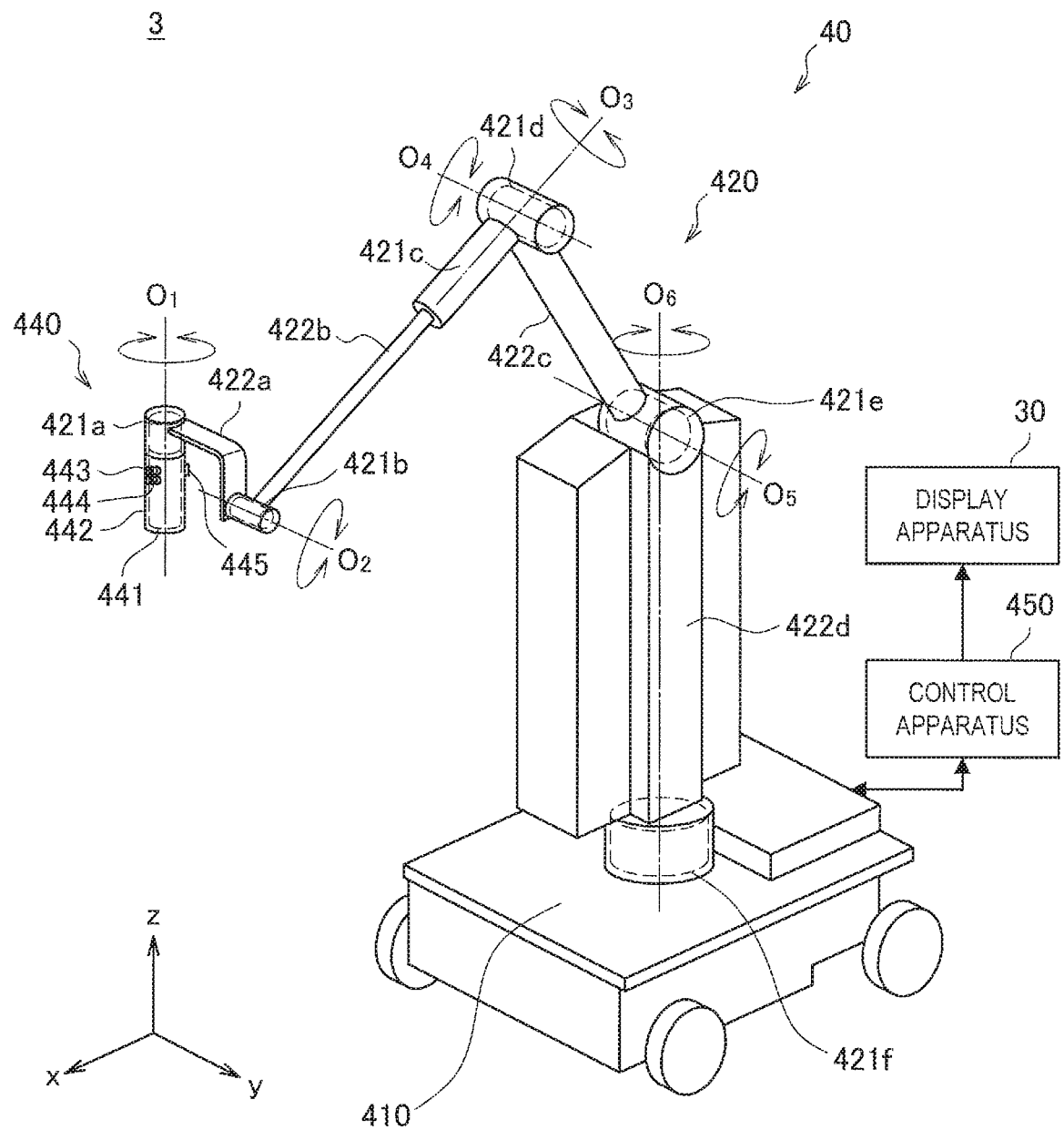
FIG. 22 is a diagram schematically illustrating a configuration of an observation system according to a third embodiment.

The configuration of an observation system according to a third embodiment of the present disclosure, and an observation apparatus that forms the observation system, will be described with reference to FIG. 22. FIG. 22 is a view illustrating a configuration of the observation system schematically according to the third embodiment.

Referring to FIG. 22, the observation system 3 according to the third embodiment includes a microscope apparatus 40 that includes a microscope section 440 and captures an image of a surgical site of a patient that is an object to be observed with the microscope section 440, and a display apparatus 30 that displays the image of the surgical site captured by the microscope apparatus 40. During surgery, the surgeon observes the subject's eye and performs various procedures on the subject's eye, while referring to the image captured by the microscope apparatus 40 and displayed on the display apparatus 30.

(Display Apparatus)

Under control of a control apparatus 450 of the microscope apparatus 40 described later, the display apparatus 30 displays the image of the subject's eye captured by the microscope apparatus 40. The display apparatus 30 is installed in a location visible to the surgeon in an operating room, such as on a wall of the operating room, for example. The type of the display apparatus 30 is not particularly limited, and any of various publicly known types of display apparatus may be used as the display apparatus 30, such as a cathode ray tube (CRT) display apparatus, a liquid crystal display apparatus, a plasma display apparatus, or an electroluminescence (EL) display apparatus. Additionally, the display apparatus 30 is not necessarily required to be installed inside the operating room, and may also be mounted onboard a device used by being worn on the surgeon's body, such as a head-mounted display (MID) or an eyeglasses-type wearable device.

Note that, as will be described later, in a case in which an imaging section 441 of the microscope section 440 of the microscope apparatus 40 is configured as a stereo camera, or such that high-resolution imaging is possible, a display apparatus 30 capable of 3D display or capable of displaying an image with high resolution may be used accordingly.

(Microscope Apparatus)

The microscope apparatus 40 is provided with a microscope section 440 for performing magnified observation of a subject's eye, an arm section 420 (holding section 420) that holds the microscope section 440, a base section 410 to which the base end of the holding section 420 is connected and which supports the microscope section 440 and the holding section 420, and a control apparatus 450 that controls the operations of the observation system 3 and the microscope apparatus 40.

(Base Section)

The base section 410 is the base of the microscope apparatus 40, and the arm section 420 extends from the base section 410. The base section 230 has a configuration and functions that are substantially the same as the base section 130 according to the first embodiment.

(Microscope Section)

The microscope section 440 includes a microscope body for performing magnified observation of the subject's eye. The microscope section 440 has a configuration corresponding to an electronic imaging microscope, and includes a barrel section 442 having an approximately cylindrical shape, and an imaging section 441 provided inside the barrel section 442. The imaging section 441 includes an optical system and an image sensor. The optical system includes optical elements such as a zoom lens, a focus lens, or other lenses, and a mirror. The image sensor captures an image of an observation target, namely the subject's eye, with light transmitted through the optical system.

The aperture on the bottom end of the barrel section 442 is provided with a cover glass for protecting the imaging section 441. A light source is also provided inside the barrel section 442, and during image capture, the subject's eye is irradiated with illuminating light radiating from the light source through the cover glass. Of this illuminating light, the light reflecting back from the subject's eye (observation light) is incident on the imaging section 441 via the cover glass, and as a result, a signal relating to the image of the subject's eye (image signal) is acquired by the imaging section 441. Note that to obtain a favorable red reflex, in the microscope section 440, the illumination optical axis and the observation optical axis are substantially coaxial.

For the imaging section 441, it is sufficient to apply a configuration implemented in any of various publicly known types of electronic imaging microscope sections, and for this reason a detailed description thereof will be reduced or omitted herein. For example, any of various publicly known types of image sensors may be applied as the image sensor of the imaging section 441, such as a charge-coupled device (CCD) sensor or a complementary metal-oxide-semiconductor (CMOS) sensor. Additionally, the imaging section 441 may also be configured as a stereo camera equipped with a pair of image sensors. Also, any of various publicly known types of configurations may be applied to the optical system of the imaging section 441. Furthermore, any of various types of functions typically provided in electronic imaging microscope sections, such as an autofocus (AF) function, an automatic exposure (AE) function, and an optical zoom function, may be provided onboard the imaging section 441.

Also, the imaging section 441 may be configured such that high-resolution imaging, such as 4K or 8K imaging, for example, is possible. Having the imaging section 441 be configured such that high-resolution imaging is possible enables an image to be displayed on the display apparatus 30 with a large screen of 50 inches or more, for example, while ensuring a predetermined resolution (for example, Full HD image quality), so visibility by the surgeon improves. Also, the predetermined resolution is able to be ensured even when an image is displayed after having been suitably magnified by an electronic zoom function. Therefore, there is no longer a need for the optical zoom function at a high magnification in the microscope section 440, so the optical system of the microscope section 440 is able to be simpler. Consequently, the microscope section 440 can be made smaller.

The image signal acquired by the microscope section 440 is transmitted to the control apparatus 450. Various kinds of image processing, such as gamma correction, white balance adjustment, and magnification and inter-pixel correction relating to the electronic zoom function and the like, for example, are performed on the image signal in the control apparatus 450. With this image processing, various kinds of image processing typically performed to display an image in a display device may be performed. The image signal that has undergone the various kinds of image processing is transmitted to the display apparatus 30 provided in the operating room, and an image of the surgical site is appropriately magnified at the desired magnification by the optical zoom function and/or the electronic zoom function, for example, and displayed on the display apparatus 30. Note that communication between the control apparatus 450 and the display apparatus 30 may be realized by any of various publicly known wired or wireless methods.

Note that the above image processing does not necessarily have to be executed by the control apparatus 450. For example, a processing circuit for executing the above image processing may also be provided in the microscope section 440. In this case, image signal which has been subjected to appropriate image processing in the processing circuit installed in the microscope section 440 may be transmitted from the microscope section 440 to the display apparatus 30. In this case, the communication between the microscope section 440 and the display apparatus 30 preferably is realized by any of various publicly known wired or wireless methods.

The microscope section 440 is provided with various types of switches for controlling the operation of the microscope section 440. For example, the microscope section 440 is provided with a zoom switch 443 (zoom SW 443) and a focus switch 444 (focus SW 444) for adjusting the image capture parameters of the microscope section 440, as well as an operating mode toggle switch 445 (operating mode toggle SW 445) for toggling the operating mode of the arm section 420.

The surgeon, by operating the zoom SW 443 and the focus SW 444, is able to perform adjusting the magnification and focusing of the microscope section 440, respectively. Also, by operating the operating mode toggle SW 445, the surgeon is able to toggle the operating mode of the holding section 420 between a locked mode and a free mode.

Herein, the locked mode is an operating mode in which the position and the attitude of the microscope section 440 are affixed by using a brake to restrain rotation about each rotation axis provided in the holding section 420. The free mode is an operating mode in which the brake is released, thereby allowing free rotation about each rotation axis provided in the holding section 420. For example, in the free mode, it is possible to adjust the position and the attitude of the microscope section 440 with direct operations by the surgeon. Herein, direct operations mean operations in which the surgeon grips the microscope section 440 with his or her hand, for example, and directly moves the microscope section 440. For example, the operating mode of the holding section 420 becomes the free mode while the surgeon is pressing the operating mode toggle SW 445, and the operating mode of the holding section 420 becomes the locked mode while the surgeon releases his or her hand from the operating mode toggle SW 445.

Note that these switches are not necessarily required to be provided on the microscope section 440. In the third embodiment, it is sufficient for the microscope apparatus 40 to be provided with a mechanism for accepting instruction input having functions similar to these switches, and the specific configuration of such a mechanism is not limited. For example, these switches may also be provided on another section of the microscope apparatus 40 in a form of a footswitch or the like. As another example, an input apparatus such as a remote control, a foot switch or the like may be used, and commands corresponding to these switches may be input into the microscope apparatus 40 remotely.

Also, although the barrel section 442 of the microscope section 440 is illustrated as a simple cylindrically-shaped member in FIG. 1 for the sake of simplicity, the barrel section 442 may also be provided with a grip section gripped by the surgeon. Such a grip section may be realized by having a structure such as a handle to be gripped by the surgeon be formed around the outer circumference of the barrel section 442. Alternatively, such a grip section may be realized by having the shape of the barrel section 442 be formed into a shape that is gripped easily by the surgeon. For example, as described above, when in the free mode, operations of moving the microscope section 440 with the surgeon gripping the barrel section 442 directly in hand may be anticipated. At this point, since the surgeon performs an operation of moving the microscope section 440 while pressing the operating mode toggle SW 445, the shape of the barrel section 442 and the placement of the operating mode toggle SW 445 may be determined appropriately with consideration for operability by the surgeon while in the free mode. In addition, the placement of the zoom SW 443 and the focus SW 444 may be determined appropriately with similar consideration for operability by the surgeon.

(Holding Section)

The holding section 420 moves the microscope section 440 three-dimensionally, while also securely supporting the position and the attitude of the microscope section 440 after moving. Specifically, the holding section 420 includes multiple rotation axis sections 421a, 421b, 421c, 421d, 421e, 421f, and multiple links 422a, 422b, 422c, 422d rotatably joined to each other by the rotation axis sections 421a to 421e. The holding section 420 is provided with six rotation axes (first axis $O_1$, second axis $O_2$, third axis $O_2$, fourth axis $O_4$, fifth axis $O_5$, and sixth axis $O_6$) corresponding to these six rotation axis sections 421a to 421f, and six degrees of freedom are realized with respect to the moving of the microscope section 440.

The links 422a to 422d are approximately rod-shaped members, in which one end of the link 422d is joined to the base section 410 via the rotation axis section 421f, the other end of the link 422a is joined to one end of the link 422c via the rotation axis section 421e, and additionally, the other end of the link 422c is joined to one end of the link 422b via the rotation axis sections 421d and 421c. Furthermore, the other end of the link 422b is joined to one end of the approximately L-shaped link 422a via the rotation axis section 421b, while the other end of the link 422a and the microscope section 440 are joined via the rotation axis section 421a. In this way, the base section 410 acts as a fulcrum, and the ends of the multiple links 422a to 422d are joined to each other by the rotation axis sections 421a to 421f, thereby configuring an arm shape extending from the base section 410.

The rotation axis sections 421a to 421f are each provided with an actuator 430 illustrated in FIG. 23 to be described later, and the rotation axis sections 421a to 421f are configured to be rotatable about a certain rotation axis according to the driving of the actuator 430. The driving of the actuator 430 is controlled by the control apparatus 450. By respectively controlling the driving of the actuator 430 in each of the rotation axis sections 421a to 421f, driving of the holding section 420 is controlled so as to extend or contract (fold up) the holding section 420, for example.

Specifically, by controlling rotation about the first axis $O_1$, rotation about the optical axis of the microscope section 440 is controlled. Also, by controlling each of rotation about the second axis $O_2$ and third axis $O_2$, the direction of the optical axis of the microscope section 440 with respect to the horizontal plane is controlled. In this way, the first axis $O_1$, the second axis $O_2$, and the third axis $O_2$ on the front end side may be considered to be the rotation axes that primarily may control the attitude (the direction of the optical axis) of the microscope section 440. In other words, by controlling the rotation of the rotation axis sections 421a to 421c corresponding to these rotation axes, primarily the attitude of the microscope section 440 may be controlled. On the other hand, the fourth axis $O_4$, the fifth axis $O_5$, and the sixth axis $O_6$ on the root side may be considered to be the rotation axes that primarily may control the three-dimensional position of the microscope section 440. In other words, by controlling the rotation of the rotation axis sections 421d to 421f corresponding to these rotation axes, primarily the position of the microscope section 440 may be controlled.

Note that in the illustrated example, as above, the holding section 420 is configured such that six degrees of freedom are realized with respect to the driving of the microscope section 440. By configuring the holding section 420 to have six degrees of freedom, the microscope section 440 can be moved freely within the movable range of the holding section 420. With this arrangement, the microscope section 440 can be made to take any position and attitude, making it possible to dispose the microscope section 440 in various directions with respect to the subject's eye in correspondence with the eye axis direction of the subject's eye. However, in the third embodiment, the configuration of the holding section 420 is not limited to the illustrated example. It is sufficient for the holding section 420 to be configured such that the microscope section 440 is able to move appropriately according to the use, while the numbers of the rotation axis sections 421a to 421f and the links 422a to 422d, their arrangement, the directions of the drive shafts of the rotation axis sections 421a to 421f, and the like may be set appropriately such that the holding section 420 has the desired degrees of freedom.

(Control Apparatus)

The control apparatus 450 includes a processor such as a central processing unit (CPU) or a digital signal processor (DSP), or a control board or the like on which these processors and a storage element such as memory are mounted together. As a result of a processor included in the control apparatus 450 executing computational processing in accordance with a predetermined program, each function in the control apparatus 450 is realized.

In the third embodiment, force control is used as the control method of the microscope apparatus 40. With force control, the force acting on the holding section 420 is detected by a torque sensor of the actuators 430 provided in each of the rotation axis sections 421a to 421f. On the basis of the detected force, a generated torque that needs to be generated by the actuators 430 provided in each of the rotation axis sections 421a to 421f in order for the holding section 420 to perform a desired movement is computed, and this computed generated torque is used as a control value to control the movement of the holding section 420.

For example, with force control, the driving of the actuators 430 may be controlled and the movement of the holding section 420 may be controlled by the control apparatus 450 in response to a direct operation by the surgeon, that is, an operation in which the surgeon touches the holding section 420 and/or the microscope section 440 directly to move the holding section 420 and/or the microscope section 440, such that the holding section 420 moves in the direction of the force imparted to the holding section 420 (in other words, to support the operation by the surgeon). In this way, by using force control, the surgeon is able to move the holding section 420 and/or the microscope section 440 while touching the holding section 420 and/or the microscope section 440 directly with smaller force, thereby making easier and more intuitive operations possible.

Note that in the third embodiment, the control apparatus 450 may also control the driving of the holding section 420 on the basis of operating other than the direct operation by the surgeon described above. For example, in accordance with instruction input performed by the surgeon via any of various types of input apparatus such as a footswitch, the control apparatus 450 may control the driving of the actuators 430 provided in each of the rotation axis sections 421a to 421f, and cause the holding section 420 to move. Alternatively, the observation system 3 may be provided with a navigation apparatus that issues instructions related to the movement of the microscope section 440 to the microscope apparatus 40. In this case, upon receiving an instruction from the navigation apparatus, the control apparatus 450 may control the driving of the actuators 430 provided in each of the rotation axis sections 421a to 421f, and cause the holding section 420 to move such that the position and the attitude of the microscope section 440 indicated by the instruction are achieved. Note that any of various publicly known types of apparatus used when moving a microscope section in a typical microscope apparatus may be used as the input apparatus or the navigation apparatus above.

Additionally, the control apparatus 450 may control various operations in the observation system 3 other than driving control of the holding section 420. For example, the control apparatus 450 includes a function of toggling the operating mode of the holding section 420 described above by controlling the driving of the brakes provided in each of the rotation axis sections of the holding section 420 in response to instruction input performed by the surgeon via the above operating mode toggle SW 445. Also, for example, the control apparatus 450 includes a function of appropriately driving the optical system of the imaging section 441 of the microscope section 440 to adjust the magnification and the focusing of the microscope section 440 in response to instruction input performed by the surgeon via the above zoom SW 443 and focus SW 444. Also, for example, the control apparatus 450 includes a function of performing various types of image processing on image signal acquired by the microscope section 440, and causing the display apparatus 30 to display an image based on the processed image signal. In other words, the control apparatus 450 also functions as a camera control unit (CCU).

Note that in the illustrated example, the control apparatus 450 is provided as a separate configuration from the microscope section 440, the holding section 420, and the base section 410, however, the third embodiment is not limited to such an example. For example, a processor, a control board, or the like that realizes functions similar to the control apparatus 450 may also be disposed inside the base section 410. Alternatively, by incorporating a processor, a control board, or the like that realizes functions similar to the control apparatus 450 into the microscope section 440 internally, the control apparatus 450 and the microscope section 440 may be configured in an integrated manner. Alternatively, functions similar to the functions of the control apparatus 450 may be realized by a processor or a control board or the like being arranged in each of the rotation axis sections 421a to 421f that form the holding section 420 of the microscope apparatus 40, and having these plurality of processors or control boards or the like work together.

Figure 23:
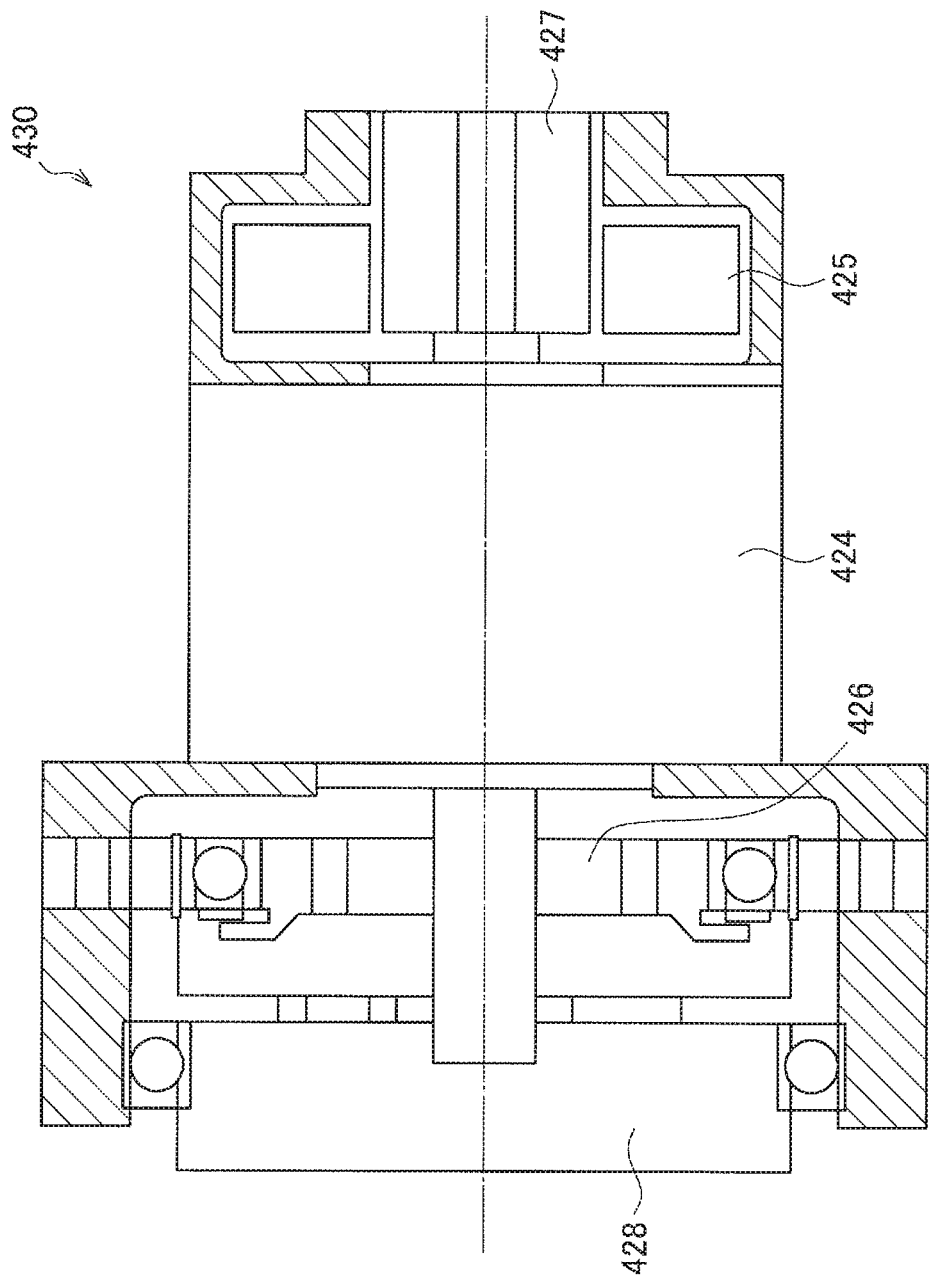
FIG. 23 is a cross-section diagram illustrating one exemplary configuration of an actuator provided in the rotation axis sections of the microscope apparatus illustrated in FIG. 22.

Here, FIG. 23 will be referenced to describe a configuration of the actuators provided in the rotation axis sections 421a to 421f of the microscope apparatus 40 illustrated in FIG. 22. FIG. 23 is a cross-section diagram illustrating an exemplary configuration of the actuators provided in the rotation axis sections 421a to 421f of the microscope apparatus 10 illustrated in FIG. 22. FIG. 2 illustrates a cross-section view of the actuator 430 in the case of cutting on a plane that goes through the rotation axis.

Referring to FIG. 23, the actuator 430 includes a motor 424, a motor driver 425, a reduction gear 426, an encoder 427, and a torque sensor 428. The actuator 430 is an actuator corresponding to force control. In the actuator 430, the rotation of the motor 424 is reduced by the reduction gear 426 at a predetermined reduction ratio, and transmitted to other members downstream via an output shaft, thereby causing the other members to be driven.

The motor 424 is a driving mechanism that, in a case of being given a certain command value (current command value), causes a rotating shaft to rotate at a rotational velocity corresponding to the command value, and thereby produces driving force. For the motor 424, a brushless motor is used, for example. However, the third embodiment is not limited to such an example, and any of various publicly known types of motors may be used as the motor 424.

The motor driver 425 is a driver circuit (driver integrated circuit (IC)) that rotationally drives the motor 424 by supplying current to the motor 424, and is able to control the rotation rate of the motor 424 by adjusting the amount of current supplied to the motor 424. The motor driver 425 drives the motor 424 by supplying the motor 424 with a current corresponding to the later-described torque command value computed by the control apparatus 450.

The reduction gear 426 is joined to the rotating shaft (drive shaft) of the motor 424. The reduction gear 426 reduces by a certain reduction ratio the rotational velocity of the rotating shaft of the joined motor 424 (in other words, the rotational velocity of the input shaft), and transmits to the output shaft. In the third embodiment, the configuration of the reduction gear 426 is not limited to a specific configuration, and any of various publicly known types of reduction gears may be used as the reduction gear 426. However, for the reduction gear 426, it is preferable to use one capable of accurately setting the reduction ratio, such as a Harmonic Drive (registered trademark), for example. In addition, the reduction ratio of the reduction gear 426 may be set appropriately according to the application of the actuator 430. For example, in the case of applying the actuator 430 to the rotation axis sections 421a to 421f of the microscope apparatus 40 as in the third embodiment, a reduction gear 426 having a reduction ratio of approximately 1:100 may be used favorably.

The encoder 427 detects the rotational angle of the input shaft (that is, the rotational angle of the rotating shaft of the motor 424). On the basis of the rotation rate of the input shaft detected by the encoder 427, and the reduction ratio of the reduction gear 426, information such as the rotational angle, the rotational angular velocity, and the rotational angular acceleration of the rotation axis sections 421a to 421f may be obtained. For the encoder 427, any of various publicly known types of rotary encoders, such as a magnetic encoder or an optical encoder, for example, may be used. Note that in the illustrated example, the encoder 427 is provided only on the input shaft of the actuator 430, but an encoder for detecting the rotational angle of the output shaft of the actuator 430 additionally may be provided farther downstream than the reduction gear 426.

The torque sensor 428 is connected to the output shaft of the actuator 430, and detects the torque acting on the actuator 430. The torque sensor 428 detects the torque output by the actuator 430 (generated torque). Additionally, the torque sensor 428 is also able to detect external torque imparted to the actuator 430 from the outside (for example, torque imparted from the outside by the surgeon in a direct operation).

Note that the configuration illustrated in FIG. 23 merely illustrates one exemplary configuration of the actuator 430 according to the third embodiment, and the third embodiment is not limited to such an example. For the actuator 430, it is possible to use any of various publicly known types of actuators typically used in an apparatus whose movement is controlled by force control.

The above describes the configuration of the observation system 3 and the microscope apparatus 40 according to the third embodiment.

(3-2. Operations of Microscope Apparatus)

As described above, in the microscope apparatus 40, the operation of the holding section 420 is controlled by force control. With force control, by appropriately setting a purpose of motion and a constraint condition, it is possible to make the holding section 420 operate causing the microscope section 440 to perform a pivot operation. In other words, in the third embodiment, a tilting section may be realized by the holding section 420. Herein, an overview of the control of the operation of the holding section 420 in the microscope apparatus 40 will be described, while in addition, details about the control when causing a pivot operation to be performed will be described.

The operation of the holding section 420 by force control in the microscope apparatus 40 are performed according to the following procedure. First, the control apparatus 450 acquires information expressing the state of each of the rotation axis sections 421a to 421f. Herein, the state of each of the rotation axis sections 421a to 421f means the state of motion of each of the rotation axis sections 421a to 421f The state of each of the rotation axis sections 421a to 421f includes information such as the rotational angle, the rotational angular velocity, and the rotational angular acceleration of each of the rotation axis sections 421a to 421f as well as the torque acting on each of the rotation axis sections 421a to 421f (including the generated torque generated by each of the rotation axis sections 421a to 421f themselves and the external torque acting on each of the rotation axis sections 421a to 421f from the outside), for example. In the microscope apparatus 40, information expressing the state of each of the rotation axis sections 421a to 421f is transmitted to the control apparatus 450 continually on a predetermined interval.

The information expressing the state of each of the rotation axis sections 421a to 421f is acquired by the encoder 427 and the torque sensor 428 of the actuator 430 provided in each of the rotation axis sections 421a to 421f. For example, in the case in which the surgeon attempts to move the microscope section 440 by a direct operation, the rotational angle, external torque, and the like in each of the rotation axis sections 421a to 421f produced in association with the direct operation on the microscope section 440 by the surgeon are detected by the encoder 427 and the torque sensor 428, and information about these detection results is transmitted to the control apparatus 450.

Next, the control apparatus 450 acquires the state of the holding section 420 on the basis of the information expressing the state of each of the rotation axis sections 421a to 421f. Herein, the state of the holding section 420 means the state of motion of the holding section 420. For example, the state of the holding section 420 includes information such as the position, velocity, acceleration, and force of the holding section 420. By acquiring the state of the holding section 420, the current position and the attitude of the holding section 420 and the microscope section 440, as well as the current force acting on the holding section 420, and the like may be grasped.

The control apparatus 450 is provided with a storage section that stores various information processed by the control apparatus 450, and an internal model of the holding section 420 and the microscope section 440 is stored in the storage section. Herein, an internal model refers to a control model used in driving control of the microscope apparatus 40, and includes information expressing the position and the attitude of the holding section 420 and the microscope section 440 to be controlled, as well as information about the motion of the holding section 420 and the microscope section 440. The control apparatus 450 is able to acquire the current state of the holding section 420 by updating the internal model on the basis of the information expressing the state of each of the rotation axis sections 421a to 421f.

Next, the control apparatus 450 sets an operation condition for calculating the torque (generated torque) to be generated by each of the rotation axis sections 421a to 421f for controlling the operation of the holding section 420 (that is, for controlling the operation of each of the rotation axis sections 421a to 421f). As the operation condition, a purpose of motion (also called a task) and a constraint condition on calculating the generated torque are set.

Herein, the purpose of motion expresses a target in the driving control of the holding section 420. For example, "maintain viewpoint of microscope section 440", "pivot operation", or the like may be set as the purpose of motion. In actual control, more specifically, target values for the position, velocity, acceleration, force, impedance, and the like of the holding section 420 for achieving these purposes of motion may be set.

Also, the constraint condition is a constraint condition related to the position, velocity, acceleration, force, and the like of the holding section 420, which are determined by the shape and structure of the holding section 420, the environment surrounding the holding section 420, settings set by the user, and the like. For example, the constraint condition includes information about the generated force, the priority, the presence or absence of non-driven joints, the vertical reaction force, friction weighting, a support polygon, and the like.

A constraint condition necessary to realize each purpose of motion may be set appropriately according to each purpose of motion. For example, if the purpose of motion is "maintain viewpoint of microscope section 440", geometric restrictions are imposed as the constraint condition on the front end position (fingertip position) and front end attitude (fingertip attitude) of the holding section 420, such that the fingertip position and the fingertip attitude are maintained in a predetermined state. Also, for example, if the purpose of motion is "pivot operation", geometric restrictions are imposed as the constraint condition on the position and the attitude of the Microscope section 440, such that the position of the microscope section 440 is positioned on a hemisphere centered on the pivot point and also such that the optical axis of the microscope section 440 is pointed in the direction of the pivot point.

Next, the control apparatus 450 computes the necessary generated torque demanded of each of the rotation axis sections 421a to 421f to achieve the purpose of motion, on the basis of the acquired state of the holding section 420 as well as the set purpose of motion and constraint condition. For example, the state of the holding section 420 includes information about the force (external torque) imparted to the holding section 420 by the surgeon in a direct operation. The control apparatus 450 takes the current position and attitude of the holding section 420 and the microscope section 440 into account to compute the generated torque demanded of each of the rotation axis sections 421a to 421f according to the force imparted to the holding section 420 by the surgeon such that the holding section 420 may be made to operate such that the purpose of motion may be achieved under the set constraint condition. For example, if the purpose of motion is "pivot operation", the control apparatus 450 takes the current position and attitude of the holding section 420 and the microscope section 440 into account to compute the generated torque demanded of each of the rotation axis sections 421a to 421f according to the force imparted to the holding section 420 by the surgeon such that the microscope section 440 is made to operate under the constraint condition described above (geometric restrictions on the position and the attitude of the microscope section 440 such that the position of the microscope section 440 is positioned on a hemisphere centered on the pivot point and also such that the optical axis of the microscope section 440 is pointed in the direction of the pivot point).

Since any of various known methods typically used in force control may be used as the specific method of computing the generated torque, a detailed description is omitted here. For example, the method using generalized inverse dynamics described in WO/2015/046081 previously submitted by the applicant may be applied as the method.

Additionally, the control apparatus 450 causes each actuator 430 in each of the rotation axis sections 421a to 421f to operate to generate the computed generated torque. Specifically, the control apparatus 450 transmits a command value (torque command value) according to the computed generated torque to each motor driver 425 of each actuator 430, and causes each motor 424 to be operated by each motor driver 425 such that a torque corresponding to the generated torque is generated. With this arrangement, the operation of the holding section 420 is controlled such that the purpose of motion may be achieved.

The above describes an overview of the control of the operation of the holding section 420 in the microscope apparatus 40 while also describing details about the control when causing a pivot operation to be performed. As described above, in the microscope apparatus 40, by setting a purpose of motion called "pivot operation" and appropriately controlling the operation of the holding section 420 such that the purpose of motion may be achieved, it becomes possible to make the microscope section 440 perform a pivot operation. Note that in pivot operations in the microscope apparatus 40, by setting the constraint condition appropriately, both a pivot operation with a fixed distance between the microscope section 210 and the pivot point and a pivot operation with a variable distance between the microscope section 210 and the pivot point may be achieved.

In the third embodiment, such a microscope apparatus 40 is used to perform eye surgery in a state with the pivot point set to the approximate center of the interior of the subject's eye. With this arrangement, similarly to the first embodiment and the second embodiment, it becomes possible to smoothly perform an operation of tilting the microscope section 440 such that a favorable red reflex is obtained in correspondence with the movement of the subject's eye. Furthermore, according to the third embodiment, at this time, since it is possible to select whether to lock the distance between the microscope section 440 and the pivot point to a fixed value or make the distance variable, by appropriately switching between these alternatives depending on the situation, movement of the microscope section 440 with a higher degree of freedom during a pivot operation can be realized. Therefore, it becomes possible to improve convenience for the surgeon further.

Note that likewise in the microscope apparatus 40, similarly to the second embodiment, whether or not to perform a pivot operation (that is, what kind of purpose of motion to set as the purpose of motion) preferably is switched appropriately by instruction input by the surgeon through an input apparatus such as a switch, for example. For example, at the setting stage before starting surgery, rather than setting "pivot operation" as the purpose of motion, a purpose of motion allowing the microscope section 210 to be moved freely is set. With this arrangement, the surgeon is able to move the microscope section 210 freely, making it possible to dispose the microscope section 210 at a suitable position with respect to the subject's eye. Subsequently, setting ends, surgery is started, and it is sufficient to set "pivot operation"

as the purpose of motion while in the middle of observing the subject's eye with the microscope section 210. With this arrangement, during surgery, smooth movement of the microscope section 440 that tracks the movement of the subject's eye may be achieved.

Note that a more detailed configuration and functions of the microscope apparatus 40 described above can be found by referencing the description in WO/2015/046081 above.

(4. Supplement)

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the above embodiments, the tilt reference point (pivot point) is substantially centered on the interior of the subject's eye, but the present technology is not limited to such an example. It is sufficient to set the tilt reference point (pivot point) at some location of the subject's eye, which may be any position. However, to obtain a favorable red reflex even after performing an operation of tilting the microscope section 110, 210, or 440, it is desirable for the eye axis of the subject's eye and the illumination optical axis to be aligned as much as possible and also for the eye axis of the subject's eye and the observation optical axis to be aligned as much as possible when the microscope section 110, 210, or 440 is tilted. From this perspective, setting the tilt reference point (pivot point) to the approximate center of the interior of the subject's eye like in the embodiments described above is thought to be preferable.

Also, in the embodiments above, the illumination optical system is provided inside the microscope section 110, 210, or 440, but the present technology is not limited to such an example. For example, the illumination optical system may also be provided externally to the microscope section 110, 210, or 440. However, even in this case, the illumination optical system and the microscope section 110, 210, or 440 are configured such that the illumination optical axis and the observation optical axis are aligned. Also, during a tilting operation (pivot operation) of the microscope section, the tilting section is configured such that the illumination optical system and the microscope section 110, 210, or 440 both tilt such that the illumination optical axis and the observation optical axis both tilt treating the tilt reference point (pivot point) as a base point, in this way, in the present technology, the tilting section is not limited to one having a function of tilting only the microscope section 110, 210, or 440, and is interpreted more broadly as one having a function of tilting the illumination optical axis and the observation optical axis treating the tilt reference point (pivot point) as a base point.

Also, each configuration in each embodiment described above may be combined with each other where possible. For example, the microscope section 110 of the microscope apparatus 10 according to the first embodiment and the microscope section 210 of the microscope apparatus 20 and 20a according to the second embodiment may be replaced with an electronic imaging microscope section. Also, for example, the microscope section 440 of the microscope apparatus 40 according to the third embodiment may be replaced with an optical microscope section.

Also, for example, the configuration described in (1-5. Modification) above may be applied to the microscope apparatus 20 and 20a according to the second embodiment and the microscope apparatus 40 according to the third embodiment. In other words, in the microscope apparatus 20, 20a, and 40, a brightness detection apparatus that detects the brightness of reflected light from the fundus of the subject's eye may be provided, and on the basis of the result of detecting the brightness by the brightness detection apparatus, a pivot operation causing the microscope section to tilt according to the motion of the subject's eye such that the brightness is maximized may be performed automatically. Also, in the microscope apparatus 20, 20a, and 40, on the basis of the result of detecting the brightness by the brightness detection apparatus, a determination may be made regarding whether or not to start a pivot operation causing the microscope section to tilt according to the motion of the subject's eye.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A microscope apparatus including:

a microscope section configured to perform magnified observation of a subject's eye while obtaining a red reflex caused by irradiating a fundus of the subject's eye with illuminating light;

a holding section configured to hold the microscope section; and a tilting section configured to tilt an illumination optical axis which is an optical axis of an illumination optical system, and an observation optical axis which is an optical axis of an observation optical system in the microscope section, around a tilt reference point in an interior of the subject's eye as a base point, while maintaining a substantially coaxial state between the illumination optical axis and the observation optical axis.

(2)

The microscope apparatus according to (1), in which the illumination optical system is provided inside the microscope section together with the observation optical system, and the tilting section causes the microscope section to operate such that the illumination optical axis and the observation optical axis tilt treating the tilt reference point as a base point.

(3)

The microscope apparatus according to (2), in which the tilting section is realized by a tilt driving mechanism that causes the microscope section to move along an arc centered on the tilt reference point.

(4)

The microscope apparatus according to (2), in which the tilting section is realized by a first rotation driving mechanism configured to support a base end of the microscope section and cause the microscope section to rotate about the illumination optical axis and the observation optical axis, a tilt driving mechanism configured to support a base end of the first rotation driving mechanism and cause the first rotation driving mechanism and the microscope section to move along an arc centered on the tilt reference point, and a second rotation driving mechanism configured to support a base end of the tilt driving mechanism and cause the tilt driving mechanism, the first rotation driving mechanism, and the microscope section to rotate.

(5)

The microscope apparatus according to (4), in which
the second rotation driving mechanism causes the tilt driving mechanism, the first rotation driving mechanism, and the microscope section to rotate about a rotation axis parallel to a direction in which the tilt driving mechanism is positioned as viewed from the second rotation driving mechanism itself.

(6)

The microscope apparatus according to (4) or (5), in which
the second rotation driving mechanism causes the tilt driving mechanism, the first rotation driving mechanism, and the microscope section to rotate such that a movement direction of the microscope section along the arc is aligned with a desired direction in which to tilt the microscope section,
the tilt driving mechanism causes the first rotation driving mechanism and the microscope section to move along the arc by a desired amount in which to tilt the microscope section, and
the first rotation driving mechanism causes the microscope section to rotate by a same amount as the rotation by the second rotation driving mechanism, in an opposite direction of a direction of the rotation by the second rotation driving mechanism.

(7)

The microscope apparatus according to (2), in which
the tilting section is realized by
an elevation apparatus configured to change a direction of the illumination optical axis and the observation optical axis by causing the microscope section to rotate about a rotation axis passing through the microscope section,
a vertical direction movement mechanism configured to cause the microscope section to move in a vertical direction, and
a horizontal plane movement mechanism configured to cause the microscope section to move in a horizontal plane.

(8)

The microscope apparatus according to (7), in which
the vertical direction movement mechanism is a linear motion mechanism causing the microscope section to move in the vertical direction, and
the horizontal plane movement mechanism is an x-y apparatus causing the microscope section to move in the horizontal plane.

(9)

The microscope apparatus according to (7), in which
the vertical direction movement mechanism is at least one rotation axis section treating a horizontal direction orthogonal to an extension direction of the holding section as a rotation axis direction from among rotation axis sections included in the holding section, and
the horizontal plane movement mechanism is at least two rotation axis sections treating a vertical direction as a rotation axis direction from among the rotation axis sections included in the holding section.

(10)

The microscope apparatus according to (2), in which
the holding section includes links rotatably connected to each other in succession by rotation axis sections such that there are at least six degrees of freedom with respect to an operation of the microscope section,
the tilting section is realized by the holding section, and
an operation of tilting the illumination optical axis and the observation optical axis by the tilting section is realized by using force control to control an operation of each of the rotation axis sections under a predetermined purpose of motion and constraint condition such that a pivot operation is achieved.

(11)

The microscope apparatus according to any one of (1) to (10), further including:
a brightness detection apparatus configured to detect a brightness of reflected light from a fundus of the subject's eye of the illuminating light; and
a control section configured to control an operation of the tilting section on the basis of a result of detecting the brightness by the brightness detection apparatus, such that the illumination optical axis and the observation optical axis tilt treating the tilt reference point as a base point such that the brightness is maximized.

(12)

The microscope apparatus according to (11), in which
the control of the operation of the tilting section by the control section is started and stopped in accordance with instruction input by a user through an input apparatus.

(13)

The microscope apparatus according to (11), in which
the control section causes the tilting section to perform the operation of tilting the illumination optical axis and the observation optical axis in a case in which a time during which the brightness is equal to or less than a predetermined threshold value exceeds a fixed time, on the basis of the result of detecting the brightness by the brightness detection apparatus.

(14)

A control method, executed by a process, including:
when using a microscope apparatus provided with a microscope section and a holding section to perform magnified observation of a subject's eye by the microscope section while obtaining a red reflex caused by irradiating the subject's eye with illuminating light,
tilting an illumination optical axis which is an optical axis of an illumination optical system, and an observation optical axis which is an optical axis of an observation optical system in the microscope section, around a tilt reference point in an interior of the subject's eye as a base point, while maintaining a substantially coaxial state between the illumination optical axis and the observation optical axis, according to a motion of the subject's eye.

REFERENCE SIGNS LIST 3 observation system
10, 20, 20a, 40 microscope apparatus
30 display apparatus
110, 210, 440 microscope section
111, 161, 171, 181 housing
112 light source
113 illumination optical system
114 observation optical system
115 eyepiece
116 objective lens
117 prism
120, 220, 220a, 420 holding section (arm section)
130, 230, 410 base section
140 footswitch
150 tilting section
160 second rotation driving mechanism
170 first rotation driving mechanism
180 tilt driving mechanism
190, 190a control section
191 driving amount computation section 192 driving control section
195 brightness detection apparatus
224, 280 linear motion mechanism
240 footswitch
260 x-y apparatus
270 elevation apparatus
450 control apparatus
503 subject's eye

The invention claimed is:

1. A microscope apparatus comprising:
a microscope section configured to perform magnified observation of a subject's eye while obtaining a red reflex caused by irradiating a fundus of the subject's eye with illuminating light;
a holding section configured to hold the microscope section; and
a tilting section configured to tilt both an illumination optical axis which is an optical axis of an illumination optical system, and an observation optical axis which is an optical axis of an observation optical system in the microscope section based on movement of the subject's eye, around a point in an interior of the subject's eye as a tilt reference point, while maintaining a substantially coaxial state between the illumination optical axis and the observation optical axis.

2. The microscope apparatus according to claim 1, wherein
the illumination optical system is provided inside the microscope section together with the observation optical system, and
the tilting section causes the microscope section to operate such that the illumination optical axis and the observation optical axis tilt around the tilt reference point as a base point.

3. The microscope apparatus according to claim 2, wherein
the tilting section is realized by a tilt driving mechanism that causes the microscope section to move along an arc centered on the tilt reference point.

4. The microscope apparatus according to claim 2, wherein
the tilting section is realized by
a first rotation driving mechanism configured to support a base end of the microscope section and cause the microscope section to rotate about the illumination optical axis and the observation optical axis,
a tilt driving mechanism configured to support a base end of the first rotation driving mechanism and cause the first rotation driving mechanism and the microscope section to move along an arc centered on the tilt reference point, and
a second rotation driving mechanism configured to support a base end of the tilt driving mechanism and cause the tilt driving mechanism, the first rotation driving mechanism, and the microscope section to rotate.

5. The microscope apparatus according to claim 4, wherein
the second rotation driving mechanism causes the tilt driving mechanism, the first rotation driving mechanism, and the microscope section to rotate about a rotation axis parallel to a direction in which the tilt driving mechanism is positioned as viewed from the second rotation driving mechanism itself.

6. The microscope apparatus according to claim 4, wherein
the second rotation driving mechanism causes the tilt driving mechanism, the first rotation driving mechanism, and the microscope section to rotate such that a movement direction of the microscope section along the arc is aligned with a desired direction in which to tilt the microscope section,
the tilt driving mechanism causes the first rotation driving mechanism and the microscope section to move along the arc by a desired amount in which to tilt the microscope section, and
the first rotation driving mechanism causes the microscope section to rotate by a same amount as the rotation by the second rotation driving mechanism, in an opposite direction of a direction of the rotation by the second rotation driving mechanism.

7. The microscope apparatus according to claim 2, wherein
the tilting section is realized by
an elevation apparatus configured to change a direction of the illumination optical axis and the observation optical axis by causing the microscope section to rotate about a rotation axis passing through the microscope section,
a vertical direction movement mechanism configured to cause the microscope section to move in a vertical direction, and
a horizontal plane movement mechanism configured to cause the microscope section to move in a horizontal plane.

8. The microscope apparatus according to claim 7, wherein
the vertical direction movement mechanism is a linear motion mechanism causing the microscope section to move in the vertical direction, and
the horizontal plane movement mechanism is an x-y apparatus causing the microscope section to move in the horizontal plane.

9. The microscope apparatus according to claim 7, wherein
the vertical direction movement mechanism is at least one rotation axis section treating a horizontal direction orthogonal to an extension direction of the holding section as a rotation axis direction from among rotation axis sections included in the holding section, and
the horizontal plane movement mechanism is at least two rotation axis sections treating a vertical direction as a rotation axis direction from among the rotation axis sections included in the holding section.

10. The microscope apparatus according to claim 2, wherein
the holding section includes links rotatably connected to each other in succession by rotation axis sections such that there are at least six degrees of freedom with respect to an operation of the microscope section,
the tilting section is realized by the holding section, and
an operation of tilting the illumination optical axis and the observation optical axis by the tilting section is realized by using force control to control an operation of each of the rotation axis sections under a predetermined purpose of motion and constraint condition such that a pivot operation is achieved.

11. The microscope apparatus according to claim 1, further comprising:
a brightness detection apparatus configured to detect a brightness of reflected light from a fundus of the subject's eye of the illuminating light; and
a control section configured to control an operation of the tilting section on a basis of a result of detecting the brightness by the brightness detection apparatus, such that the illumination optical axis and the observation optical axis tilt around the tilt reference point such that the brightness is maximized.

12. The microscope apparatus according to claim 11, wherein
the control of the operation of the tilting section by the control section is started and stopped in accordance with instruction input by a user through an input apparatus.

13. The microscope apparatus according to claim 11, wherein
the control section causes the tilting section to perform the operation of tilting the illumination optical axis and the observation optical axis in a case in which a time during which the brightness is equal to or less than a predetermined threshold value exceeds a fixed time, on a basis of the result of detecting the brightness by the brightness detection apparatus.

14. A control method, executed by a process, comprising:
when using a microscope apparatus provided with a microscope section and a holding section to perform magnified observation of a subject's eye by the microscope section while obtaining a red reflex caused by irradiating the subject's eye with illuminating light,
tilting both an illumination optical axis which is an optical axis of an illumination optical system, and an observation optical axis which is an optical axis of an observation optical system in the microscope section based on movement of the subject's eye, around a point in an interior of the subject's eye as a tilt reference point, while maintaining a substantially coaxial state between the illumination optical axis and the observation optical axis, according to a motion of the subject's eye.

15. The control method according to claim 14, further comprising:
detecting a brightness of reflected light from a fundus of the subject's eye of the illuminating light; and
controlling tilting on a basis the brightness, such that the illumination optical axis and the observation optical axis tilt around the tilt reference point such that the brightness is maximized.

16. The control method according to claim 15, further comprising
on condition that the brightness is equal to or less than a predetermined threshold for a period greater than or equal to a fixed time, automatically controlling tilting.

17. The control method according to claim 14, further comprising
controlling tilting based on a user input.

18. A non-transitory computer readable storage device having computer readable instructions that when executed by circuitry cause the circuitry to:
when using a microscope to perform magnified observation of a subject's eye by the microscope while obtaining a red reflex caused by irradiating the subject's eye with illuminating light,
tilt both an illumination optical axis which is an optical axis of an illumination optical system, and an observation optical axis which is an optical axis of an observation optical system, different from the illumination optical system, in the microscope based on movement of the subject's eye, around a point in an interior of the subject's eye as a tilt reference point, while maintaining a substantially coaxial state between the illumination optical axis and the observation optical axis.

19. The non-transitory computer readable storage device having computer readable instructions according to claim 18, further causing the circuitry to:
control the tilt on a basis of a brightness of reflected light from a fundus of the subject's eye of the illuminating light, such that the illumination optical axis and the observation optical axis tilt around the tilt reference point such that the brightness is maximized.

20. The non-transitory computer readable storage device having computer readable instructions according to claim 19, further causing the circuitry to:
tilt the illumination optical axis and the observation optical axis in a case in which a time during which the brightness is equal to or less than a predetermined threshold value exceeds a fixed time.

* * * * *